(12) United States Patent
Berggren et al.

(10) Patent No.: US 8,021,853 B2
(45) Date of Patent: Sep. 20, 2011

(54) INHIBITION OF THE β3 SUBUNIT OF L-TYPE CA$^{2+}$ CHANNELS

(75) Inventors: Per-Olof Berggren, Solna (SE); Veit Flockerzi, Bierback (DE)

(73) Assignee: BioCrine AB, Stockholm (SE)

( * ) Notice: Subject to any disclaimer, the term of this patent is extended or adjusted under 35 U.S.C. 154(b) by 460 days.

(21) Appl. No.: 11/510,105

(22) Filed: Aug. 25, 2006

(65) Prior Publication Data

US 2007/0003533 A1    Jan. 4, 2007

Related U.S. Application Data

(63) Continuation of application No. 10/392,810, filed on Mar. 19, 2003, now abandoned.

(60) Provisional application No. 60/366,152, filed on Mar. 20, 2002, provisional application No. 60/442,142, filed on Jan. 22, 2003.

(51) Int. Cl.
| | |
|---|---|
| *G01N 33/567* | (2006.01) |
| *C12N 15/63* | (2006.01) |
| *C12N 15/85* | (2006.01) |
| *C07K 5/00* | (2006.01) |
| *C07H 21/04* | (2006.01) |

(52) U.S. Cl. .................. 435/7.21; 435/320.1; 435/325; 530/300; 536/23.1; 514/866

(58) Field of Classification Search .................. None
See application file for complete search history.

(56) References Cited

U.S. PATENT DOCUMENTS

| 6,242,200 B1 | 6/2001 | Wilkison et al. |
|---|---|---|
| 6,361,995 B1 | 3/2002 | Konrad |

FOREIGN PATENT DOCUMENTS

| EP | 0 556 651 | 8/1993 |
|---|---|---|
| JP | 8009969 | 1/1996 |
| WO | WO 95/04822 | 2/1995 |
| WO | WO 98/11131 | 3/1998 |
| WO | WO 00/02543 | 1/2000 |
| WO | WO 01/30137 | 5/2001 |
| WO | WO 02/45498 | 6/2002 |

OTHER PUBLICATIONS

Wu et al., J Pharmacol Exp Ther 292: 939-943, 2000.*
Rutter et al. Cell Calcium 16: 71-80, 1994.*
Wang et al. Am J Physiol Heart Circ Physiol 278: H714-H722, 2000.*
Berggren et al. Cell 119: 273-284, 2004.*
Stephens et al. Eur J Physiol 433: 523-532, 1997.*
Meir et al Biophys Jour 79: 731-746, 2000.*
Berggren & Larsson, (1994), Biochem. Soc. Transact., "Ca$^{2+}$ and pancreatic β-cell function", vol. 22, pp. 12-18.
Michael J. Berridge, (1998), Neuron, "Neuronal calcium signaling", vol. 21, pp. 13-26.
Colvin, et al., (1982), J. Cardiovasc. Pharmacol., "Efects of Ca channel blockers on Ca transport and Ca ATPase in skeletal and cardiac sarcoplasmic reticulum vesicles", vol. 4(6), pp. 935-941.
De Koninck, et al., (1998), Science, "Sensitivity of CaM kinase II to the frequency of Ca2+ oscillations", vol. 279, pp. 227-230.
Dolmetsch, et al., (1997), Nature, "Differential activation of transcription factors induced by Ca2+ response amplitude and duration", vol. 386, pp. 855-858.
Hajnoczky, et al., (1995), Cell, "Decoding of cytosolic calcium oscillations in the mitochondria", vol. 82, pp. 415-424.
Hamill, O.P., et al., (1981), Pfugers Arch., "Improved patch-clamp techniques for high-resolution current recording from cells and cell-free membrane patches", vol. 391, pp. 85-100.
Hoth, M., et al., . (1993), J. Physiol., "Calcium release-activated calcium current in rat mast cells", vol. 456, pp. 359-386.
Hullin, et al., (1992), EMBO J., Calcium channel β subunit heterogeneity: functional expression of cloned cDNA from heart, aorta and brain, vol. 11 (3), pp. 885-890.
Ihara, et al., (1995), Mol. Endocrinol., "molecular diversity and functional characterization of voltage-dependent calcium channels (CACN4) expressed in pancreatic β-cells", vol. 9, pp. 121-130.
Kostyuk, et al., (1982), J. Membrane Biol., "surface charges on the outer side of mollusk neuron membrane", vol. 70, pp. 171-179.
Murakami, et al., (1996), Eur. J. Biochem., "Gene structure of the murine calcium channel β 3 subunit, cDNA and characterization of alternative splicing and transcription products", vol. 236, pp. 138-143.
Nagy, A., et al., (1993), Proc. Natl. Acad. Sci., "Derivation of completely cell culture-derived mice from early-passage embryonic stem cells", USA, vol. 90, pp. 8424-8428.
Olcese, et al., (1994), Neuron, "The amino terminus of a calcium channel β subunit sets rates of channel inactivation independently of the subunit's effect on activation", vol. 13, pp. 1433-1438.
James W. Putney, Jr., (1986), Cell Calcium, "A model for receptor-regulated calcium entry", vol. 7, pp. 1-12.
Roe, et al., (1993), J. Biol. Chem., "Voltage-dependent intracellular calcium release from mouse islets stimulated by glucose", vol. 268, pp. 9953-9956.
Roe, et al., (1998), J. Biol. Chem., "Characterization of a Ca2+ release-activated nonselective cation current regulating membrane potential and [Ca$^{2+}$], oscillations in transgenically derived β cells", vol. 273, pp. 10402-10410.
Rosati, et al., (2000), FASEB J., "Glucose-and arginine-induced insulin secretion by human pancreatic β-cells: the role of HERG K$^+$ channels in firing and release", vol. 14, pp. 2601-2610.

(Continued)

*Primary Examiner* — Ali R. Salimi
*Assistant Examiner* — Aditi Dutt
(74) *Attorney, Agent, or Firm* — McDonnell Boehnen Hulbert & Berghoff LLP

(57) ABSTRACT

The present invention provides reagents and methods for identifying inhibitors of the L-type Ca$^{2+}$ channel β$_3$ protein, which has been demonstrated to be involved in calcium signaling, insulin secretion, and glucose homeostasis. The invention also provides therapeutics and methods for treating a subject with one or more of diabetes, insulin resistance, impaired insulin secretion, and impaired glucose homeostasis, involving the use of inhibitors of an L-type Ca$^{2+}$ channel β$_3$ subunit to provide a benefit to the subject.

8 Claims, 2 Drawing Sheets

OTHER PUBLICATIONS

Singer, et al., (1991), Science, "The Roles of the subunits in the function of the calcium channel", vol. 253, pp. 1553-1557.

Smith, et al., Annals New York academy of sciences, "Neuronal Voltage-activated calcium channels: on the roles of the $\alpha_{1E}$ and $\beta_3$ subunits", pp. 175-198.

Tareilus, et al., (1997), Proc. Natl. Acad. Sci. USA, "A *Xenopus oocyte* β subunit evidence for a role in the assembly/expression of voltage-gated calcium channels that is separate from its role as a regulatory subunit", vol. 94, pp. 1703-1708.

Welling A., et al., (1993), Journal of Physiology, "Stable co-expression of calcium channel alpha1, beta and alpha2/delta subunits in a somatic cell line", vol. 471, pp. 749-765.

Welling A., et al., (1995), Pfluegers Archiv European Journal of Physiology, "Expression of the L-type calcium channel with two different beta subunits and its modulation by RO40-5967", vol. 429(3), pp. 400-411.

Yamada, Y, et al., (1995), Genomics, "The structures of the human calcium channel alpha1 subunit (CACNL1A2) and beta subunit (CACNLB3) genes", vol. 27(2), pp. 312-319.

Zaitsev, S.V., et al., (1995), Proc. Natl. Acad. Sci. USA, "Dissociation between changes in cytoplasmic free Ca2+ concentration and insulin secretion as evidenced from measurements in mouse single pancreatic islets", vol. 92, pp. 9712-9716.

* cited by examiner

β3-GENE

TARGETING VECTOR

TARGETING EVENT

SEQUENCE LISTING

<160> NUMBER OF SEQ ID NOS: 8

<210> SEQ ID NO 1
<211> LENGTH: 2469
<212> TYPE: DNA
<213> ORGANISM: Mus musculus

<400> SEQUENCE: 1
gggcgcggcg ccgtcctcgc ccgcgctcgc tcccccacc caccccggac tccccatgt    60

```
atgacgactc ctacgtgccc gggtttgagg actcggaggc gggttcagcc gactcctaca    120
ccagccgccc ctctctggac tcagacgtct ccctggagga ggaccgggag agtgcccggc    180
gagaagtgga gagtcaggct cagcagcagc tggaaagagc caagcacaaa cctgtggcat    240
ttgctgtgag gaccaatgtc agctactgtg gggttctgga tgaggagtgc ccggtccagg    300
cctctggagt caactttgag gccaaagatt ttctgcacat aaagagaag tacagcaatg    360 actggtggat cgggaggcta gtgaaagaag gcggagcaat cgccttcatc cccagccccc    420
aacgcctgga gagcatccgc ctcaaacagg aacagaaggc caggagatct gggaaccctt    480
ccagcctggg tgacattggc ttccgacgct ctcctcctcc gtctctagcc aagcagaagc    540
aaaagcaggc ggaacatgtt cccccgtatg atgtggtgcc ctccatgcgg cctgtggtgc    600
tggtgggacc ctctctgaaa ggctatgagg tcacggacat gatgcagaag gcgctcttcg    660
acttccttaa acacaggttt gatggcagga tctccatcac acgcgtcacg gccgacctct    720
cgctggccaa gcgctctgtg ctcaacaatc ctggcaagag gaccatcatt gagcgctcct    780
ccgcccgctc cagcattgct gaagtgcaga gtgagattga gcgcatattc gagctggcca    840
aatccctgca gctagtggtg ttggatgctg acaccatcaa ccacccagca caacttgcca    900
agacctcact ggctcccatc atcgtctttg tcaaagtgtc ctcgccaaag gtactgcagc    960
gactgatccg atccagggga aagtcacaga tgaagcacct cactgtacag atgatgcgt   1020 acgataagct ggttcagtgc ccacccgagt cattcgacgc gattctggat gagaaccagc   1080
tagaagatgc ctgtgagcac ctggctgaat acttagaggt ttactggcga gcgacccacc   1140
acccagcacc gggccccgga ctgctgggtc cgcctagtgc catccctgga cttcagaacc   1200
agcagcagct gggggagcga gtggaggagc actcaccct ggagagggac agcctgatgc   1260
cctcagatga ggccagcgag agctcccgcc aggcctggac cggatcttca cagcgcagct   1320
ctcgccatct ggaggaggac tatgcagatg cctaccagga cctgtaccag cctcaccgcc   1380
aacacacctc ggggctgccc agtgctaacg ggcacgaccc ccaagaccgg ctcctagccc   1440
aggactcgga gcatgaccac aatgaccgga actggcagcg taaccggcct tggcccaagg   1500
acagctactg accacctcct gccccaccct ggcaggcgca ggcacagcgg ctggggtgtc   1560
cacctcaggc aggttggagt tagattggca ttaggctgcc gttagttcag ctcacacaac   1620
cctctgccca gccccaggtc cagggctgac tgtggtccca aggttctggg agaagcaagg   1680 ggccctcac ctcctgggca cagtgacccc gtaggttctc atccgggtac tagccgtgtt   1740
ctgcatcctt ggcacctccc cctgcataag ctgccgcccc cgtgggcaac aatctcaggc   1800
caggatcact tagcaggggc cttccagcca gaatggatgc ccctctaaag agcaagaggg   1860
tgtgagtgtg ggcaacatag cctgaggaag aagaaactcg gttcctaagc aggtgtagat   1920
cctaagcaaa gggactccat tcacgccact gccacacatc agaaatgaag caatcagagc   1980
tcaacatggc ggcacttctg tcccatcagc tggggtgggc acttacacct aagacaggag   2040
cagtgcgggt gaggcaggac agacagactc acagctgtag ctctgctaga aaacggggga   2100
ctcaaccaaa ccgggaggct tagcatctgg tgagactggg gaactggggc atattcaagc   2160
caagagccag cctggactgg gggggagggt gggacagctt ccggccccc ttgctcttct   2220 cattctttgc ccttgcatct gtcatttctg tcctttccct ccatggctcc tgcaagatag   2280
gggcttcctg actcatagca gccacttcag ttagggttag atgagaggaa caggacacag   2340
tgaacagccc ccgaggctgt ccacctggct acccttgcct tatggctcta gcgtgtgacc   2400
tacagagcat gctccattaa gaacccgccc cacctcattg tcatctccaa taaaacacca   2460
``` cgcacagtc                                                         2469

<210> SEQ ID NO 2
<211> LENGTH: 484
<212> TYPE: PRT
<213> ORGANISM: Mus musculus

<400> SEQUENCE: 2

Met Tyr Asp Asp Ser Tyr Val Pro Gly Phe Glu Asp Ser Glu Ala Gly
1               5                   10                  15

Ser Ala Asp Ser Tyr Thr Ser Arg Pro Ser Leu Asp Ser Asp Val Ser
            20                  25                  30

Leu Glu Glu Asp Arg Glu Ser Ala Arg Arg Glu Val Glu Ser Gln Ala
        35                  40                  45

Gln Gln Gln Leu Glu Arg Ala Lys His Lys Pro Val Ala Phe Ala Val
    50                  55                  60

Arg Thr Asn Val Ser Tyr Cys Gly Val Leu Asp Glu Glu Cys Pro Val
65                  70                  75                  80

Gln Ala Ser Gly Val Asn Phe Glu Ala Lys Asp Phe Leu His Ile Lys
                85                  90                  95

Glu Lys Tyr Ser Asn Asp Trp Trp Ile Gly Arg Leu Val Lys Glu Gly
            100                 105                 110

Gly Ala Ile Ala Phe Ile Pro Ser Pro Gln Arg Leu Glu Ser Ile Arg
        115                 120                 125

Leu Lys Gln Glu Gln Lys Ala Arg Arg Ser Gly Asn Pro Ser Ser Leu
    130                 135                 140

Gly Asp Ile Gly Phe Arg Ser Pro Pro Ser Leu Ala Lys Gln
145                 150                 155                 160

Lys Gln Lys Gln Ala Glu His Val Pro Pro Tyr Asp Val Val Pro Ser
                165                 170                 175

Met Arg Pro Val Val Leu Val Gly Pro Ser Leu Lys Gly Tyr Glu Val
            180                 185                 190

Thr Asp Met Met Gln Lys Ala Leu Phe Asp Phe Leu Lys His Arg Phe
        195                 200                 205

Asp Gly Arg Ile Ser Ile Thr Arg Val Thr Ala Asp Leu Ser Leu Ala
    210                 215                 220

Lys Arg Ser Val Leu Asn Asn Pro Gly Lys Arg Thr Ile Ile Glu Arg
225                 230                 235                 240

Ser Ser Ala Arg Ser Ile Ala Glu Val Gln Ser Glu Ile Glu Arg
                245                 250                 255

Ile Phe Glu Leu Ala Lys Ser Leu Gln Leu Val Val Leu Asp Ala Asp
            260                 265                 270

Thr Ile Asn His Pro Ala Gln Leu Ala Lys Thr Ser Leu Ala Pro Ile
        275                 280                 285

Ile Val Phe Val Lys Val Ser Ser Pro Lys Val Leu Gln Arg Leu Ile
    290                 295                 300

Arg Ser Arg Gly Lys Ser Gln Met Lys His Leu Thr Val Gln Met Met
305                 310                 315                 320

Ala Tyr Asp Lys Leu Val Gln Cys Pro Pro Glu Ser Phe Asp Ala Ile
                325                 330                 335

Leu Asp Glu Asn Gln Leu Glu Asp Ala Cys Glu His Leu Ala Glu Tyr
            340                 345                 350

Leu Glu Val Tyr Trp Arg Ala Thr His His Pro Ala Pro Gly Pro Gly
        355                 360                 365

```
Leu Leu Gly Pro Pro Ser Ala Ile Pro Gly Leu Gln Asn Gln Gln Gln
        370                 375                 380

Leu Gly Glu Arg Val Glu Glu His Ser Pro Leu Glu Arg Asp Ser Leu
385                 390                 395                 400

Met Pro Ser Asp Glu Ala Ser Glu Ser Ser Arg Gln Ala Trp Thr Gly
                405                 410                 415

Ser Ser Gln Arg Ser Ser Arg His Leu Glu Glu Asp Tyr Ala Asp Ala
                420                 425                 430

Tyr Gln Asp Leu Tyr Gln Pro His Arg Gln His Thr Ser Gly Leu Pro
            435                 440                 445

Ser Ala Asn Gly His Asp Pro Gln Asp Arg Leu Leu Ala Gln Asp Ser
        450                 455                 460

Glu His Asp His Asn Asp Arg Asn Trp Gln Arg Asn Arg Pro Trp Pro
465                 470                 475                 480

Lys Asp Ser Tyr

<210> SEQ ID NO 3
<211> LENGTH: 2525
<212> TYPE: DNA
<213> ORGANISM: Rattus norvegicus

<400> SEQUENCE: 3
cgggggcggc gcggctcggt ggcatctcgg gcgcggcccg ccgtcctcgc ccccggcgcc      60
gctcgctccc cccaccccac cccggactcc cccatgtatg acgactccta cgtgcccggg     120
tttgaggact cggaggcggg ttcagccgac tcctacacca gccgcccctc tctggactca     180
gacgtttccc tggaggagga ccgggagagt gcccggcgag aagtggagag tcaggctcag     240
cagcagctgg aaagagccaa gcacaaacct gtggcatttg ctgtgaggac caatgtcagc     300
tactgtggag ttctggatga ggaatgccca gtccagggct ctggagtcaa cttcgaggcc     360
aaagattttc tgcacattaa agagaagtac agcaatgact ggtggatcgg aggctagtg      420 aaagaaggtg gcgatattgc cttcatcccc agcccccaac gcctggagag catccggctc     480
aaacaggaac agaaggccag gagatccggg aaccccttcca gctgagtga cattggcaac      540 cgacgttccc ctcctccatc tctagccaag cagaagcaaa agcaggcgga acatgtcccc     600
ccgtatgatg tggtgccctc catgcggcct gtggtgctgg tgggaccctc tctgaaaggt     660
tatgaggtca cagacatgat gcagaaggct ctcttcgact tccttaaaca caggtttgat     720
ggcaggatct ccatcacccg cgtcacggct gaccctctcac tggccaagcg ctctgtgctc     780
aacaatcctg gcaagaggac catcatcgag cgctcttctg cccgctccag cattgctgag     840
gtgcagagtg agattgagcg catattcgag ctggccaaat ccctgcagct agtggtgttg     900
gatgctgaca ccatcaacca cccagcacag ctagccaaga cctcactggc ccccatcatc     960
gtcttcgtca agtgtcctc gccaaaggta ctgcagcgac tgatccgctc caggggaag    1020 tcccagatga agcacctcac tgtacagatg atggcatatg ataagctggt tcagtgccca    1080
cctgagtcat tgatgtgat tctggatgag aaccagctgg acgacgcctg tgagcaccta    1140
gctgaatacc tagaggttta ctggcgcgct acccaccacc cagcaccggg ccccgggatg    1200
ctgggtccgc ccagtgccat ccctggactt cagaaccagc agctgctggg ggagcgaggt    1260
gaggagcatt caccctgga gcgggacagt ttgatgccct cggatgaggc cagtgagagc    1320
tcccgccagg cctggaccgg atcttcacag cgcagctccc gccatctgga ggaggactat    1380
gcagatgcct accaggacct gtaccagcct caccgtcaac acacctcggg gctacccagt    1440
gctaacgggc atgacccca agaccggctc ctagcccagg actcggagca tgaccacaat    1500
```

```
gaccggaact ggcagcgtaa ccggccttgg cctaaggaca gctactgacc acctcctgcc    1560
ctaccctggc aggcacagac acagcggctg gggtgtccac ctcaggcagg ttggagttag    1620
attggcgtta ggctgcctct aggttcagct cacacaaccc tctgcccagc cctaggtcca    1680
gggctgactg tggtcccaag gttctgggag aagcaagggg ccccctcacc tcctgggcac    1740
agtgaccccg taggttctca tccaggtact agctgtgttc tgcatccttg cgccttccc    1800 ctgcataaga agctgccccg gtgagcaatg atctcaggcc gggatcactt agcagggtc    1860 ttccagccag aatggatacc cctctaaaca gcaggagggt gtgagtgcag caatgtagc    1920 atgaggaaga gacatggttc ctgagcaggc gtaaaccta agcaaaggaa ctccgttcac    1980
gtcactgccg cacattagaa atgaagcaat cagagctcaa catggcggca cttctatccc    2040
atcagctggg gtgggcactt acacctaaga caggagcagt gcaggtgagg caggacagac    2100
agctcatggc tgtagctctg ttagagaacg gccctcctca ccaaaccagg aagcttagca    2160
tctggcaaga ctagggaact ggggcacagt caagcccaaa gccggcctgg actgcgggga    2220 aggggggagca gcttccagcc ccccacccc ccttgctttc ctcattcttt gcccttgcgt    2280
ctgtcatttc tgttccttcc ctccatgcct cctgcaagat aggggctccc tggctcgtag    2340
ctgccacttg ttaagttagg gttagatgag aggaacagac acaatgaaca gccccagagg    2400
ctgtcacctg ctaccttg ccttatggct ctagcgtttg acctacagag catgctccat    2460
taagaacccg cccacctca ttgtcatctc caataaaaca taacgcacag tcccttgggt    2520
gtctc                                                                2525

<210> SEQ ID NO 4
<211> LENGTH: 484
<212> TYPE: PRT
<213> ORGANISM: Rattus norvegicus

<400> SEQUENCE: 4

Met Tyr Asp Asp Ser Tyr Val Pro Gly Phe Glu Asp Ser Glu Ala Gly
1               5                   10                  15

Ser Ala Asp Ser Tyr Thr Ser Arg Pro Ser Leu Asp Ser Asp Val Ser
            20                  25                  30

Leu Glu Glu Asp Arg Glu Ser Ala Arg Arg Glu Val Glu Ser Gln Ala
        35                  40                  45

Gln Gln Gln Leu Glu Arg Ala Lys His Lys Pro Val Ala Phe Ala Val
    50                  55                  60

Arg Thr Asn Val Ser Tyr Cys Gly Val Leu Asp Glu Glu Cys Pro Val
65                  70                  75                  80

Gln Gly Ser Gly Val Asn Phe Glu Ala Lys Asp Phe Leu His Ile Lys
                85                  90                  95

Glu Lys Tyr Ser Asn Asp Trp Trp Ile Gly Arg Leu Val Lys Glu Gly
            100                 105                 110

Gly Asp Ile Ala Phe Ile Pro Ser Pro Gln Arg Leu Glu Ser Ile Arg
        115                 120                 125

Leu Lys Gln Glu Gln Lys Ala Arg Arg Ser Gly Asn Pro Ser Ser Leu
    130                 135                 140

Ser Asp Ile Gly Asn Arg Arg Ser Pro Pro Ser Leu Ala Lys Gln
145                 150                 155                 160

Lys Gln Lys Gln Ala Glu His Val Pro Tyr Asp Val Val Pro Ser
                165                 170                 175

Met Arg Pro Val Val Leu Val Gly Pro Ser Leu Lys Gly Tyr Glu Val
            180                 185                 190
```

Thr Asp Met Met Gln Lys Ala Leu Phe Asp Phe Leu Lys His Arg Phe
        195                 200                 205

Asp Gly Arg Ile Ser Ile Thr Arg Val Thr Ala Asp Leu Ser Leu Ala
        210                 215                 220

Lys Arg Ser Val Leu Asn Asn Pro Gly Lys Arg Thr Ile Ile Glu Arg
225                 230                 235                 240

Ser Ser Ala Arg Ser Ser Ile Ala Glu Val Gln Ser Glu Ile Glu Arg
                245                 250                 255

Ile Phe Glu Leu Ala Lys Ser Leu Gln Leu Val Val Leu Asp Ala Asp
            260                 265                 270

Thr Ile Asn His Pro Ala Gln Leu Ala Lys Thr Ser Leu Ala Pro Ile
        275                 280                 285

Ile Val Phe Val Lys Val Ser Ser Pro Lys Val Leu Gln Arg Leu Ile
        290                 295                 300

Arg Ser Arg Gly Lys Ser Gln Met Lys His Leu Thr Val Gln Met Met
305                 310                 315                 320

Ala Tyr Asp Lys Leu Val Gln Cys Pro Pro Glu Ser Phe Asp Val Ile
                325                 330                 335

Leu Asp Glu Asn Gln Leu Asp Asp Ala Cys Glu His Leu Ala Glu Tyr
            340                 345                 350

Leu Glu Val Tyr Trp Arg Ala Thr His His Pro Ala Pro Gly Pro Gly
        355                 360                 365

Met Leu Gly Pro Pro Ser Ala Ile Pro Gly Leu Gln Asn Gln Gln Leu
        370                 375                 380

Leu Gly Glu Arg Gly Glu Glu His Ser Pro Leu Glu Arg Asp Ser Leu
385                 390                 395                 400

Met Pro Ser Asp Glu Ala Ser Glu Ser Ser Arg Gln Ala Trp Thr Gly
                405                 410                 415

Ser Ser Gln Arg Ser Ser Arg His Leu Glu Glu Asp Tyr Ala Asp Ala
            420                 425                 430

Tyr Gln Asp Leu Tyr Gln Pro His Arg Gln His Thr Ser Gly Leu Pro
        435                 440                 445

Ser Ala Asn Gly His Asp Pro Gln Asp Arg Leu Leu Ala Gln Asp Ser
        450                 455                 460

Glu His Asp His Asn Asp Arg Asn Trp Gln Arg Asn Arg Pro Trp Pro
465                 470                 475                 480

Lys Asp Ser Tyr

<210> SEQ ID NO 5
<211> LENGTH: 1717
<212> TYPE: DNA
<213> ORGANISM: Homo sapiens

<400> SEQUENCE: 5

```
tcccccacc  ccaccccgga  ctcccccatg  tatgacgact  cctacctgcc  cgggtttgag    60
gactcggagg  cgggttcagc  cgactcctac  accagccgcc  catctctgga  ctcagacgtc   120
ctggaggagg  accgggagag  tgcccggcgt  gaagtagaga  gccaggctca  gcagcagctc   180
gaaagggcca  agcacaaacc  tgaggcattt  gcggtgagga  ccaatgtcag  ctactgtggc   240
gtactggatg  aggagtgccc  agtccagggc  tctggagtca  actttgaggc  caaagatttc   300
ctccacatta  agagaagta  cagcaatgac  tggtggatcg  gcggctagt  gaaagagggc   360 ggggacatcg  ccttcatccc  cagccccag  cgcctggaga  gcatccggct  caaacaggaa   420
cagaaggcca  ggagatccgg  gaaccccttc  agcctgagtg  acattggcaa  ccgacgttcc   480
```

```
cctcctccat ctctagccaa gcagaagcaa aagcaggcgg aacatgttcc cccgtatgac    540
gtggtgccct caatgcggcc ggtggtgctg gtgggaccct ctctgaaagg ttatgaggtc    600
acagacatga tgcagaaggc tctcttcgac ttcctcaaac acagatttga tggcaggatc    660
tccatcaccc gagtcacagc cgacctctcc ctggcaaagc gatctgtgct caacaatccg    720
ggcaagagga ccatcattga cgctcctct  gcccgctcca gcattgcgga agtgcagagt    780
gagatcgagc gcatatttga gctggccaaa tccctgcagc tagtagtgtt ggacgctgac    840
accatcaacc acccagcaca gctggccaag acctcgctgg ccccatcat  cgtctttgtc    900 aaagtgtcct caccaaaggt actccagcgt ctcattcgct cccggggaa  gtcacagatg    960 aagcacctga ccgtacagat ggcatatgat aagctggttc agtgcccacc ggagtcattt   1020
gatgtgattc tggatgagaa ccagctggag gatgcctgtg agctcctggc tgagtacctg   1080
gaggtttact ggcgggccac gcaccaccca gccctggcc  cggacttct  gggtcctccc   1140 agtgccatcc ccggacttca gaaccagcag ctgctggggg agcgtggcga ggagcactcc   1200 cccttgagc  gggacagctt gatgccctct gatgaggcca gcgagagctc ccgccaagcc   1260
tggacaggat cttcacagcg tacgtcccgc cacctggagg aggactacgc agatgcctac   1320
caggacctgt accagcctca ccgccaacac acctcggggc tgcctagtgc taacgggcat   1380 gaccccaag  accggcttct agcccaggac tcagaacaca accacagtga ccggaactgg   1440
cagcgcaacc gcccttggcc caaggatagc tactgacagc ctcctgctgc cctaccctgg   1500
caggcacagg cgcagctggc tgggggccc  actccaggca ggtggcgtta gactggcatc   1560
aggctggcac tagctcagcc ccccaaaccc ctgcccagc  ccagcttca  gggctgcctg   1620 tggtcccaag gttctgggag aaacagggac ccctcacct  cctgggcagt gaccctact   1680 aggctcccat tccaggtact agctgtgtgt tctcgag                            1717
```

<210> SEQ ID NO 6
<211> LENGTH: 482
<212> TYPE: PRT
<213> ORGANISM: Homo sapiens

<400> SEQUENCE: 6

```
Met Tyr Asp Asp Ser Tyr Leu Pro Gly Phe Glu Asp Ser Glu Ala Gly
1               5                   10                  15

Ser Ala Asp Ser Tyr Thr Ser Arg Pro Ser Leu Asp Ser Asp Val Leu
            20                  25                  30

Glu Glu Asp Arg Glu Ser Ala Arg Arg Glu Val Glu Ser Gln Ala Gln
        35                  40                  45

Gln Gln Leu Glu Arg Ala Lys His Lys Pro Glu Ala Phe Ala Val Arg
    50                  55                  60

Thr Asn Val Ser Tyr Cys Gly Val Leu Asp Glu Glu Cys Pro Val Gln
65                  70                  75                  80

Gly Ser Gly Val Asn Phe Glu Ala Lys Asp Phe Leu His Ile Lys Glu
                85                  90                  95

Lys Tyr Ser Asn Asp Trp Trp Ile Gly Arg Leu Val Lys Glu Gly Gly
            100                 105                 110

Asp Ile Ala Phe Ile Pro Ser Pro Gln Arg Leu Glu Ser Ile Arg Leu
        115                 120                 125

Lys Gln Glu Gln Lys Ala Arg Arg Ser Gly Asn Pro Ser Ser Leu Ser
    130                 135                 140

Asp Ile Gly Asn Arg Arg Ser Pro Pro Pro Ser Leu Ala Lys Gln Lys
145                 150                 155                 160
```

-continued

```
Gln Lys Gln Ala Glu His Val Pro Pro Tyr Asp Val Val Pro Ser Met
            165                 170                 175

Arg Pro Val Val Leu Val Gly Pro Ser Leu Lys Gly Tyr Glu Val Thr
        180                 185                 190

Asp Met Met Gln Lys Ala Leu Phe Asp Phe Leu Lys His Arg Phe Asp
            195                 200                 205

Gly Arg Ile Ser Ile Thr Arg Val Thr Ala Asp Leu Ser Leu Ala Lys
        210                 215                 220

Arg Ser Val Leu Asn Asn Pro Gly Lys Arg Thr Ile Ile Glu Arg Ser
225                 230                 235                 240

Ser Ala Arg Ser Ser Ile Ala Glu Val Gln Ser Glu Ile Glu Arg Ile
                245                 250                 255

Phe Glu Leu Ala Lys Ser Leu Gln Leu Val Val Leu Asp Ala Asp Thr
            260                 265                 270

Ile Asn His Pro Ala Gln Leu Ala Lys Thr Ser Leu Ala Pro Ile Ile
        275                 280                 285

Val Phe Val Lys Val Ser Ser Pro Lys Val Leu Gln Arg Leu Ile Arg
    290                 295                 300

Ser Arg Gly Lys Ser Gln Met Lys His Leu Thr Val Gln Met Ala Tyr
305                 310                 315                 320

Asp Lys Leu Val Gln Cys Pro Pro Glu Ser Phe Asp Val Ile Leu Asp
                325                 330                 335

Glu Asn Gln Leu Glu Asp Ala Cys Glu Leu Leu Ala Glu Tyr Leu Glu
            340                 345                 350

Val Tyr Trp Arg Ala Thr His His Pro Ala Pro Gly Pro Gly Leu Leu
        355                 360                 365

Gly Pro Pro Ser Ala Ile Pro Gly Leu Gln Asn Gln Gln Leu Leu Gly
    370                 375                 380

Glu Arg Gly Glu Glu His Ser Pro Leu Glu Arg Asp Ser Leu Met Pro
385                 390                 395                 400

Ser Asp Glu Ala Ser Glu Ser Ser Arg Gln Ala Trp Thr Gly Ser Ser
                405                 410                 415

Gln Arg Thr Ser Arg His Leu Glu Glu Asp Tyr Ala Asp Ala Tyr Gln
            420                 425                 430

Asp Leu Tyr Gln Pro His Arg Gln His Thr Ser Gly Leu Pro Ser Ala
        435                 440                 445

Asn Gly His Asp Pro Gln Asp Arg Leu Leu Ala Gln Asp Ser Glu His
    450                 455                 460

Asn His Ser Asp Arg Asn Trp Gln Arg Asn Arg Pro Trp Pro Lys Asp
465                 470                 475                 480

Ser Tyr
```

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
agcacaaacc tgtggcattt g                                          21

<210> SEQ ID NO 8
<211> LENGTH: 21
<212> TYPE: DNA
<213> ORGANISM: Artificial sequence

```
<220> FEATURE:
<223> OTHER INFORMATION: PCR primer

<400> SEQUENCE: 8
tcggttgcca atgtcaccca g                                      21
```

INHIBITION OF THE β3 SUBUNIT OF L-TYPE CA$^{2+}$ CHANNELS

CROSS REFERENCE

This application is a continuation of U.S. patent application Ser. No. 10/392,810 filed Mar. 19, 2003, now abandoned, which claims priority to U.S. Provisional Application Ser. No. 60/366,152 filed Mar. 20, 2002 and to U.S. Provisional Application Ser. No. 60/442,142 filed Jan. 22, 2003.

FIELD OF THE INVENTION

This invention relates to molecular biology, cell biology, voltage gated calcium channels, calcium signaling, drug discovery, diabetes, insulin resistance, impaired insulin secretion, and impaired glucose homeostasis.

BACKGROUND

Diabetes mellitus (DM) comprises a series of disorders, all characterized by hyperglycemia. Type I ("insulin dependent") DM is characterized by insulin deficiency, whereas Type II ("non-insulin dependent" or "adult-onset") DM is characterized by insulin resistance, impaired insulin secretion, and increased hepatic glucose production. Chronic complications of DM result from hyperglycemia and include retinopathy, neuropathy, nephropathy, and cardiovascular disease.

In the pancreatic β-cell, membrane depolarization and an oscillatory increase in $[Ca^{2+}]_i$ are key features in glucose-induced insulin secretion. The oscillatory increase in $[Ca^{2+}]_i$ is regulated by a sophisticated interplay between nutrients, hormones and neurotransmitters and is due to both $Ca^{2+}$ influx through voltage-gated L-type $Ca^{2+}$ channels and $Ca^{2+}$ mobilization from intracellular stores such as the endoplasmic reticulum (ER) (Berggren & Larsson 1994, Biochem. Soc. Transact. 22:12-18). Upon metabolism of glucose within the β-cell, ATP is formed, which in turn closes specific ATP-regulated K$^+$ channels, triggering depolarization of the plasma membrane. Such depolarization leads to an opening of voltage-gated L-type $Ca^{2+}$ channels, $Ca^{2+}$ influx, an increase in $[Ca^{2+}]_i$, and subsequently insulin release. The opening of the voltage-gated L-type $Ca^{2+}$ channels thus occurs at glucose concentration levels that stimulate pancreatic beta cells to secrete insulin.

L-type $Ca^{2+}$ channels are multi-subunit proteins, consisting of a combination of α, β, and γ subunits, where each type of subunit exists in multiple forms. While the $\alpha_1$ subunit forms the pore of the L-type $Ca^{2+}$ channel, the β subunits are believed to play a key role in the assembly/expression of the channel complex, and to modulate $Ca^{2+}$ currents through the $\beta_1$ subunits (Singer et al. 1991, Science 253:1553-1557; Hullin et al. 1992, EMBO J. 11:885-890; Tareilus et al. 1997, Proc. Natl. Acad. Sci. USA 94:1703-1708). To date the role of $Ca^{2+}$ channel β subunits in insulin secretion has mainly been studied by heterologous expression experiments (Ihara et al. 1995, Mol. Endocrinol. 9:121-130). Pancreatic β-cells express both $\beta_2$ and $\beta_3$ subunits.

Intracellular stores such as the ER are able to modulate depolarization-induced $Ca^{2+}$ signaling by sequestering some of the $Ca^{2+}$ entering through the voltage-gated L-type $Ca^{2+}$ channels into intracellular calcium stores, or by releasing additional $Ca^{2+}$ into the cytoplasm. Such $Ca^{2+}$ release may occur through $Ca^{2+}$ mediated activation of phosphatidylinositol-specific phospholipase C (PI-PLC) and formation of inositol 1,4,5-trisphosphate (Ins(1,4,5)P$_3$) or through direct gating of the intracellular $Ca^{2+}$ channels by the incoming $Ca^{2+}$.

Most efforts to develop drugs to promote insulin secretion, treat insulin resistance, and increase the efficiency of glucose homeostasis have targeted the ATP-regulated K$^+$ channels. However, such drugs often act regardless of the blood glucose concentration, and thus can lead to serious side effects, such as hypoglycemia. Therefore, there is a need in the art to identify targets for therapeutics that do not suffer from these drawbacks.

SUMMARY OF THE INVENTION

In one aspect, the present invention provides non-human transgenic animals having a disruption in the L-type $Ca^{2+}$ channel $\beta_3$ gene that inhibits expression of active L-type $Ca^{2+}$ channel $\beta_3$ protein, and methods for making such transgenic animals. In a further aspect, the present invention provides isolated nucleic acid sequences and vectors for creating such transgenic animals.

In another aspect, the present invention provides recombinant host cells that have been transfected with a recombinant expression vector comprising nucleic acid control sequences operatively linked to an L-type $Ca^{2+}$ channel $\beta_3$ gene, wherein the host cell does not possess functional L-type $Ca^{2+}$ channels.

In another aspect, the present invention provides methods for identifying inhibitors of the L-type $Ca^{2+}$ channel $\beta_3$ protein, comprising providing the recombinant host cells of the invention, contacting the recombinant host cells with a calcium indicator that emits detectable signals in the presence of calcium, treating the recombinant cells with one or more test compounds, wherein the treating occurs before, simultaneous with, or after the contacting of the recombinant host cells with the calcium indicator, stimulating the recombinant host cells with an amount of ATP that is effective to increase intracellular calcium concentration in control cells, and detecting the signals from the calcium indicator in the recombinant host cells, wherein a test compound-induced increase in the signals from the calcium indicator in the recombinant host cells indicates that the test compound is an inhibitor of the L-type $Ca^{2+}$ channel $\beta_3$ protein.

In a further aspect, the present invention provides methods for treating a subject with one or more disorders selected from the group consisting of diabetes, insulin resistance, impaired insulin secretion, and impaired glucose homeostasis, comprising administering to the subject one or more inhibitors of an L-type $Ca^{2+}$ channel $\beta_3$ subunit to provide a benefit to the subject.

DETAILED DESCRIPTION OF THE INVENTION

Figure 1A:
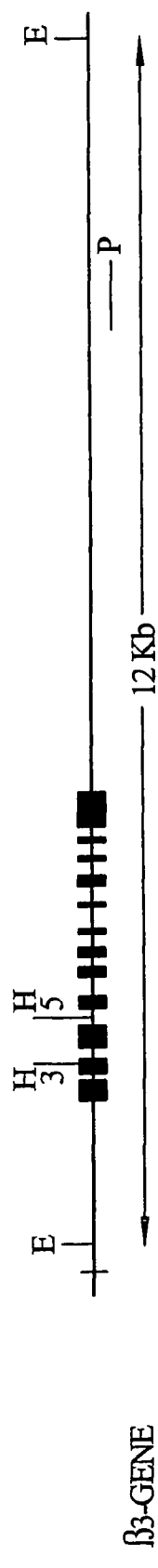
FIG. 1 depicts the organization of the $\beta_3$ gene (A) and the targeting vector (IIMB) used to generate a knockout of the $\beta_3$ gene (B). Exons are represented by filled boxes and introns by lines. The structure of the homologous recombination product is shown in (C). Abbreviations: E, EcoRI; H, HincII; P, probe; tk, herpes simplex virus thymidin kinase gene.

The present invention fulfills a need in the art by identifying the $\beta_3$ subunit of voltage-gated L-type $Ca^{2+}$ channel as a target for drugs to treat diabetes, insulin resistance, impaired insulin secretion, and impaired glucose homeostasis. The inventors have discovered that inhibition of the $\beta_3$ subunit of voltage-gated L-type $Ca^{2+}$ channel (hereinafter referred to as the "L-type $Ca^{2+}$ channel $\beta_3$ protein" or the "L-type $Ca^{2+}$ channel $\beta_3$ subunit") leads to increased secretion of insulin only at stimulatory glucose concentrations (i.e.: blood levels of glucose that are increased above normal levels, that is above about 100 mg/dL).

Therefore, inhibitors of the L-type $Ca^{2+}$ channel $\beta_3$ protein are much less likely to lead to hypoglycemia or other serious side effects than are currently available treatments for diabetes, insulin resistance, impaired insulin secretion, and impaired glucose homeostasis.

In one aspect, the invention provides a non-human transgenic animal having a disruption (i.e., "knockout") in the L-type $Ca^{2+}$ channel $\beta_3$ gene that inhibits expression of active L-type $Ca^{2+}$ channel $\beta_3$ protein wherein the non-human animal is characterized, relative to a wild type animal, by one or more characteristic selected from the group consisting of (a) an increase in calcium release from intracellular calcium stores, (b) increased insulin release at stimulatory concentrations of glucose, but not at basal glucose levels, and (c) more efficient glucose removal from blood.

The transgenic animals of the invention are useful for the determination of the function of the L-type $Ca^{2+}$ channel $\beta_3$ protein, as a source of specific cell types (for example, pancreatic $\beta$-cells) in which expression of the L-type $Ca^{2+}$ channel $\beta_3$ protein is knocked out, and for use in verifying that a candidate compound is acting as an inhibitor of the L-type $Ca^{2+}$ channel $\beta_3$ protein (discussed below).

By "increased insulin release at stimulatory concentrations of glucose, but not at basal glucose levels" it is meant that the transgenic animals of the invention will secrete more insulin than wild type animals when the blood glucose concentration rises to a stimulatory level, but not when the blood glucose concentration is at a basal level. By "more efficient glucose removal from blood" it is meant that in response to an oral or intraperitoneal glucose tolerance test, the transgenic animals of the invention will remove glucose from the bloodstream at a more efficient rate than wild type animals.

As used herein, the term "transgenic animal" refers to a non-human animal, (e.g., single-celled organism (e.g., yeast), mammal, or non-mammal (e.g., nematode or *Drosophila*)), having a non-endogenous (i.e., heterologous) nucleic acid sequence present as an extra-chromosomal element in a portion of its cells or stably integrated into its germ line DNA (i.e., in the genomic sequence of most or all of its cells), as well as the progeny of such animals. In a preferred embodiment, the transgenic animal is a mammal, and the heterologous nucleic acid sequence is stably integrated. In a more preferred embodiment, the transgenic animal is a rodent. The terms "rodent" and "rodents" refer to all members of the phylogenetic order Rodentia (including rats and mice), including any and all progeny of all future generations derived therefrom.

In a most preferred embodiment, the transgenic animal is a transgenic mouse with either a heterozygous or homozygous disruption in the L-type $Ca^{2+}$ channel $\beta_3$ gene. In a preferred embodiment, the transgenic mice have a homozygous disruption in the L-type $Ca^{2+}$ channel $\beta_3$ gene. In a most preferred embodiment, the transgenic mice of the invention have a homozygous disruption that results in a null mutation of the endogenous L-type $Ca^{2+}$ channel $\beta_3$ gene.

As used in this aspect of the invention, the "L-type $Ca^{2+}$ channel $\beta_3$ gene" and "L-type $Ca^{2+}$ channel $\beta_3$ protein" can be from any non-human animal for which an L-type $Ca^{2+}$ channel $\beta_3$ knockout is desired. In a preferred embodiment, the L-type $Ca^{2+}$ channel $\beta_3$ gene is from mouse or rat. In a most preferred embodiment, the mouse L-type $Ca^{2+}$ channel $\beta_3$ gene ([SEQ ID NO: 1], GenBank accession number U20372) is the target to be "knocked out." In another most preferred embodiment, the rat L-type $Ca^{2+}$ channel $\beta_3$ gene ([SEQ ID NO:3], GenBank accession number M88751) is the target to be "knocked out."

As used herein, a "knockout" of an L-type $Ca^{2+}$ channel $\beta_3$ gene refers to partial or complete reduction of the expression of at least a portion of the polypeptide encoded by an endogenous L-type $Ca^{2+}$ channel $\beta_3$ gene of a single cell, selected cells, or all of the cells of the animal. "Knockout" transgenics of the invention can be transgenic animals having a "heterozygous knockout," wherein one allele of the endogenous L-type $Ca^{2+}$ channel $\beta_3$ gene has been disrupted, or a homozygous knockout, wherein both alleles of the endogenous L-type $Ca^{2+}$ channel $\beta_3$ gene have been disrupted. "Knockouts" also include conditional knockouts, where alteration of the target gene can occur upon, for example, exposure of the animal to a substance that promotes target gene disruption, introduction of an enzyme that promotes recombination at the target gene site (e.g., Cre in the Cre-lox system), or any other method for disrupting the target gene alteration post-natally.

The term "progeny" refers to any and all future generations derived or descending from the transgenic animal, whether the transgenic animal is heterozygous or homozygous for the knockout construct. Progeny of any successive generation are included herein such that the progeny, the F1, F2, and F3 generations, and so on indefinitely, containing the knockout construct are included in this definition.

In a further aspect, the present invention provides isolated pancreatic islets and pancreatic $\beta$-cells that are isolated from the transgenic animals of the invention. Such isolated pancreatic beta cells possess a disruption in the L-type $Ca^{2+}$ channel $\beta_3$ gene, and thus are useful as a model of the L-type $Ca^{2+}$ channel $\beta_3$ gene knockout within a specific cell type in which the L-type $Ca^{2+}$ channel $\beta_3$ gene is normally active.

Methods for isolating pancreatic islets and $\beta$-cells are known in the art. See, for example, U.S. Pat. No. 6,361,995 and Rosati et al. 2000, *FASEB J* 14:2601-10.

In a further aspect, the present invention provides an isolated nucleic acid sequence comprising an L-type $Ca^{2+}$ channel $\beta_3$ gene knockout construct, which comprises a selectable marker sequence flanked by DNA sequences homologous to the endogenous L-type $Ca^{2+}$ channel $\beta_3$ gene. In a preferred embodiment, the L-type $Ca^{2+}$ channel $\beta_3$ gene is from mouse or rat. In a most preferred embodiment, the mouse L-type $Ca^{2+}$ channel $\beta_3$ gene ([SEQ ID NO:1], GenBank accession number U20372) is the target to be "knocked out". In another most preferred embodiment, the rat L-type $Ca^{2+}$ channel $\beta_3$ gene ([SEQ ID NO:3], GenBank accession number M88751) is the target to be "knocked out."

The term "knockout construct" refers to a nucleotide sequence that is designed to decrease or suppress expression of a polypeptide encoded by an endogenous L-type $Ca^{2+}$ channel $\beta_3$ gene in one or more cells of an animal. The nucleotide sequence used as the knockout construct is comprised of (1) DNA from some portion of the endogenous L-type $Ca^{2+}$ channel $\beta_3$ gene (one or more exon sequences, intron sequences, and/or promoter sequences) to be suppressed and (2) a selectable marker sequence used to detect the presence of the knockout construct in the cell. The knockout construct is inserted into a cell containing the endogenous L-type $Ca^{2+}$ channel $\beta_3$ gene to be knocked out. The knockout construct can then integrate within one or both alleles of the endogenous L-type $Ca^{2+}$ channel $\beta_3$ gene, and such integration of the L-type $Ca^{2+}$ channel 3 gene knockout construct can prevent or interrupt transcription of the full-length endogenous L-type $Ca^{2+}$ channel $\beta_3$ gene. Integration of the L-type $Ca^{2+}$ channel $\beta_3$ gene knockout construct into the cellular chromosomal DNA is typically accomplished via homologous recombination (i.e., regions of the L-type $Ca^{2+}$ channel $\beta_3$ gene knockout construct that are homologous or complimentary to endogenous L-type $Ca^{2+}$ channel $\beta_3$ gene DNA sequences can hybridize to each other when the knockout construct is inserted into the cell; these regions can then recombine so that the knockout construct is incorporated into the corresponding position of the endogenous DNA).

Typically, the knockout construct is inserted into an undifferentiated cell termed an embryonic stem cell (ES cell). ES cells are usually derived from an embryo or blastocyst of the same species as the developing embryo into which it can be introduced, as discussed below. In a more preferred embodiment, the knockout constructs are placed into a rodent ES cell line, most preferably a mouse ES cell line, such as mouse R1 ES cells.

By way of example, a nucleotide sequence knockout construct can be prepared by inserting a nucleotide sequence comprising an antibiotic resistance gene into a portion of an isolated nucleotide sequence comprising an L-type $Ca^{2+}$ channel $\beta_3$ gene that is to be disrupted. When this knockout construct is then inserted into ES cells, the construct can integrate into the genomic DNA of at least one L-type $Ca^{2+}$ channel $\beta_3$ allele. Thus, many progeny of the cell will no longer express L-type $Ca^{2+}$ channel $\beta_3$ protein in at least some cells, or will express it at a decreased level and/or in a truncated form, as at least part of the endogenous coding region of L-type $Ca^{2+}$ channel $\beta_3$ gene is now disrupted by the antibiotic resistance gene.

The term "selectable marker sequence" is used to identify those cells that have incorporated the L-type $Ca^{2+}$ channel $\beta_3$ gene knockout construct into their chromosomal DNA. The selectable marker sequence may be any sequence that serves this purpose, although typically it will be a sequence encoding a protein that confers a detectable trait on the cell, such as an antibiotic resistance gene, an assayable enzyme not naturally found in the cell, or a fluorescent signal (such as green fluorescent protein). The marker sequence will also typically contain either a homologous or heterologous promoter that regulates its expression.

In another aspect, the present invention provides methods for making transgenic animals that have a disruption in the L-type $Ca^{2+}$ channel $\beta_3$ gene, comprising transforming an embryonic stem cell with a knockout construct of the invention as described above, thereby producing a transformed embryonic stem cell; injecting the transformed embryonic stem cell into a blastocyst; implanting the blastocyst comprising the transformed embryonic stem cell into a pseudopregnant female animal; allowing the blastocyst to develop to term; and identifying a transgenic animal whose genome comprises a heterozygous or homozygous disruption of the endogenous L-type $Ca^{2+}$ channel $\beta_3$ gene. In a preferred embodiment, the animal is a mouse. In a most preferred embodiment, the blastocysts are mouse C57BL/6 blastocysts.

In another aspect, the present invention provides recombinant host cells that have been transfected with a recombinant expression vector comprising nucleic acid control sequences operatively linked to an L-type $Ca^{2+}$ channel $\beta_3$ coding sequence, wherein the host cell does not possess functional $\beta_3$ subunit-containing L-type $Ca^{2+}$ channels, and methods for using the recombinant host cells. In a preferred embodiment, such host cells are not derived from muscle cells, neurons, or neuro-endocrine cells. In a most preferred embodiment, the host cells of the invention undergo $InsP_3$-induced $Ca^{2+}$ release. The recombinant host cells of this aspect of the invention can contain functional L-type $Ca^{2+}$ channels that do not include the $\beta 3$ subunit. Verification that such cells do not possess functional $\beta 3$ subunit-containing L-type $Ca^{2+}$ channels can be done by techniques known to one of skill in the art, such as measuring patch-clamp electrophysiological registrations.

Such host cells are useful, for example, in drug screening assays for identifying compounds that inhibit the expression or activity of the L-type $Ca^{2+}$ channel $\beta_3$ protein.

As used herein the "L-type $Ca^{2+}$ channel $\beta_3$ coding sequence" refers to nucleic acid sequences that encode an L-type $Ca^{2+}$ channel $\beta_3$ protein from any animal, preferably from rat, mouse, or human, most preferably human. In a further preferred embodiment, the L-type $Ca^{2+}$ channel $\beta_3$ coding sequence is selected from the group consisting of nucleic acid sequences that encode mouse L-type $Ca^{2+}$ channel $\beta_3$ protein ([SEQ ID NO:2], GenBank accession number NP_031607), nucleic acid sequences that encode rat L-type $Ca^{2+}$ channel 3 protein ([SEQ ID NO:4], GenBank accession number NP_036960), and nucleic acid sequences that encode human L-type $Ca^{2+}$ channel $\beta_3$ protein ([SEQ ID NO:6], GenBank accession number NP_000716).

Such nucleic acid sequences can be DNA or RNA, but are preferably double stranded DNA sequences. Such double stranded nucleic acid sequences can comprise genomic L-type $Ca^{2+}$ channel $\beta_3$ nucleic acid sequences (and thus may include introns), or may comprise cDNA sequences devoid of any intron sequences.

The terms "host cell" and "recombinant host cell" are used interchangeably herein. It should be understood that such terms refer not only to the particular subject cell, but also to the progeny of such a cell. Since modifications may occur in succeeding generations due to either mutation or environmental influences, such progeny may not, in fact, be identical to the parent cell, but are still included within the scope of the term as used herein.

The host cells can be transiently or stably transfected with the recombinant expression vector. Such transfection of expression vectors into eukaryotic cells can be accomplished via any technique known in the art, including, but not limited to, calcium phosphate co-precipitation, electroporation, or liposome mediated-, DEAE dextran mediated-, polycationic mediated-, or viral mediated-transfection. Alternatively, the host cells can be infected with a recombinant viral expression vector. (See, for example, *Molecular Cloning: A Laboratory Manual* (Sambrook, et al., 1989, Cold Spring Harbor Laboratory Press); *Culture of Animal Cells: A Manual of Basic Technique*, $2^{nd}$ Ed. (R. I. Freshney. 1987. Liss, Inc. New York, N.Y.)). The host cells can be established cell lines, or primary cell cultures.

In a preferred embodiment, the promoter is heterologous (i.e., is not the naturally occurring L-type $Ca^{2+}$ channel $\beta 3$ gene promoter). A promoter and an L-type $Ca^{2+}$ channel $P_3$-encoding nucleic acid sequence are "operatively linked" when the promoter is capable of driving expression of the L-type $Ca^{2+}$ channel $\beta_3$ nucleic acid sequence. As used herein, the term "vector" refers to a nucleic acid molecule capable of transporting another nucleic acid to which it has been linked. One type of vector is a "plasmid," which refers to circular double stranded DNA into which additional DNA segments may be cloned. Another type of vector is a viral vector, wherein additional DNA segments may be cloned into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors".

The vector may also contain additional sequences, such as a polylinker for subcloning of additional nucleic acid sequences and a polyadenylation signal to effect proper polyadenylation of the transcript. The nature of the polyadenylation signal is not believed to be crucial to the successful practice of the invention, and any such sequence may be employed, including, but not limited to, the SV40 and bovine growth hormone poly-A sites. The vector may also comprise a termination sequence, which can serve to enhance message levels and to minimize read through from the construct into other sequences. Finally, expression vectors may include selectable markers, often in the form of antibiotic resistance genes, which permit selection of cells that carry these vectors.

As discussed above, ATP stimulates calcium release from intracellular stores. The inventors of the present invention have discovered that the L-type $Ca^{2+}$ channel $\beta_3$ protein serves to inhibit the ATP-stimulated release of calcium from intracellular stores. This inhibitory activity is not dependent on the existence of functional voltage-gated channels in the cells. Thus, in the recombinant cells of the invention disclosed above, expression of the L-type $Ca^{2+}$ channel $\beta_3$ protein serves to inhibit ATP-stimulated release of calcium from intracellular stores. Inhibitors of the L-type $Ca^{2+}$ channel $\beta_3$ protein administered to the recombinant cells of the invention serve to restore the ATP-stimulated release of calcium from intracellular stores.

Thus, in another aspect, the present invention provides methods for identifying inhibitors of the L-type $Ca^{2+}$ channel $\beta_3$ protein, comprising providing the recombinant host cells of the invention; contacting the host cells with a detectable calcium indicator, wherein the calcium indicator emits detectable signals in the presence of calcium; treating the host cells with one or more test compounds to be screened, wherein the treating occurs before, simultaneous with, or after the contacting of the host cells with the calcium indicator; stimulating the host cells with an amount of ATP that is effective to increase intracellular calcium concentration in control cells; and detecting signals from the calcium indicator in the host cells, and comparing the signals to those detected from control cells; wherein the signals are used to detect restoration of the ATP-stimulated signal in the host cells due to the contacting of the host cells with the one or more test compounds, and wherein such a restoration in response to a test compound indicates that the test compound is an inhibitor of the L-type $Ca^{2+}$ channel $\beta_3$ protein. Such restoration can include partial or complete restoration of the ATP-stimulated signal to the level seen in control cells.

As used herein, an "inhibitor" of the L-type $Ca^{2+}$ channel $\beta_3$ subunit includes compounds that inhibit the transcription of the L-type $Ca^{2+}$ channel $\beta_3$ DNA into RNA, compounds that inhibit the translation of L-type $Ca^{2+}$ channel $\beta_3$ RNA into protein, and compounds that inhibit the function of L-type $Ca^{2+}$ channel $\beta_3$ protein. Such inhibiting can be complete inhibition or partial inhibition, such that the expression and/or activity of the L-type $Ca^{2+}$ channel $\beta_3$ subunit is reduced, resulting in a reduced ability to inhibit release of calcium from intracellular calcium stores.

In a preferred embodiment, the cells are mammalian cells. In a most preferred embodiment, the cells are selected from the group consisting of rodent and human cells.

The "one or more test compounds" can be of any nature, including, but not limited to, chemical and biological compounds and environmental samples. The one or more test compounds may also comprise a plurality of compounds, including, but not limited to, combinatorial chemical libraries and natural compound libraries. Contacting the host cells with the one or more test compounds can occur before, after, and/or simultaneously with the contacting of the host cells with the detectable calcium indicator, depending on the details of the assay design. For example, in order to carry out kinetic screening, it is necessary to detect the signals from the host cells at multiple time points, and the user may acquire detectable signals before, at the time of, and after contacting of the cells with the test compound.

As used herein, the term "detectable calcium indicator" means any molecule or molecules emitting a detectable, measurable signal upon intracellular interaction with calcium. Such indicators and their use are known in the art and include, but are not limited to, calcium-sensitive bioluminescent proteins, fluorescent proteins, and synthetic probes such as fluorescent calcium dyes, such as are available, for example, from Molecular Probes (Eugene, Oreg.). In a preferred embodiment, the detectable calcium indicator is a fluorescent calcium indicator.

As used herein, a stimulatory amount of ATP for increasing intracellular calcium signaling for a given cell type can be determined routinely by one of skill in the art. For most such applications, the use of between 0.2 µM and 500 µM ATP will be effective and most preferably the amount of ATP is between 1 µM and 100 µM.

In order to derive optimal information on the ability of the one or more test compounds to inhibit L-type $Ca^{2+}$ channel $\beta_3$ expression and/or activity, it is preferred to compare the signals from the detectable calcium indicator in recombinant host cells with signals from control cells. Such control cells can include one or more of the following:

1. The same recombinant host cells, treated in the same way except not contacted with the one or more test compounds;
2. The same recombinant host cells, treated in the same way except contacted with the one or more test compounds at different time points (for analyzing time-dependent effects);
3. The same recombinant host cells, treated in the same way except contacted with different concentrations of the one or more test compounds (for analyzing concentration-dependent effects);
4. Non-recombinant cells of the same cell type as the recombinant host cells, contacted with the one or more test compounds; and
5. Non-recombinant cells of the same cell type as the recombinant host cells, not contacted with the one or more test compounds.

In a preferred embodiment of the invention, the control cells undergo $InsP_3$-induced $Ca^{2+}$ release that is diminished or inhibited by expression of the L-type $Ca^{2+}$ channel $\beta_3$ protein, wherein such $InsP_3$-induced $Ca^{2+}$ release can be restored by an inhibitor of the L-type $Ca^{2+}$ channel $\beta_3$ protein.

In a preferred embodiment, the cells are plated in microplates of 96 wells or more, and the method is conducted in a high throughput manner. After potential lead compounds are identified, various confirmatory assays can be carried out, such as examining the effect of the potential lead compound on the transgenic animals or the isolated pancreatic beta islet cells of the invention disclosed above. If the compound is acting as an inhibitor of the L-type $Ca^{2+}$ channel $\beta_3$ subunit, it will have a lesser or no effect on the transgenic animal and/or the pancreatic beta islet cells, thus verifying that the cellular target for the lead compound is the L-type $Ca^{2+}$ channel $\beta_3$ subunit.

In various preferred embodiment of this aspect of the invention, the screening methods described herein are used to identify compounds for use in treating one or more disorders selected from the group consisting of diabetes, insulin resistance, impaired insulin secretion, and impaired glucose homeostasis.

In yet another aspect, the invention provides L-type $Ca^{2+}$ channel $\beta_3$ subunit inhibitors identified by the methods described above.

In a further aspect, the present invention provides methods for treating a subject with one or more disorder selected from the group consisting of diabetes, insulin resistance, impaired insulin secretion, and impaired glucose homeostasis, comprising administering to the subject one or more inhibitors of an L-type $Ca^{2+}$ channel $\beta_3$ subunit to provide a benefit to the subject.

As used herein, the term "subject" or "patient" is meant any subject for which therapy is desired, including humans, cattle, dogs, cats, guinea pigs, rabbits, rats, mice, insects, horses, chickens, and so on. Most preferably, the subject is human.

As used herein, "diabetes" is characterized by insufficient or no production of insulin by the pancreas, leading to high blood sugar levels. In a preferred embodiment, the diabetes is Type II diabetes. For such a patient, a "benefit" includes one or more of increased insulin production and lowering of blood sugar levels.

As used herein, "impaired insulin secretion" refers to an inability to secrete adequate insulin to maintain a normal blood glucose level. For such a patient, a "benefit" includes one or more of increased insulin production, and lowering or normalizing of blood sugar levels.

As used herein, "insulin resistance" means a decreased insulin effectiveness in stimulating glucose uptake and/or restraining hepatic glucose production. For such a patient, a "benefit" includes a lowering or normalizing of blood sugar levels.

As used herein, "impaired glucose homeostasis" means an inability to maintain a normal blood glucose concentration. For such a patient, a "benefit" includes one or more of increased insulin production, lowering of blood sugar levels, and normalization of blood sugar levels over time.

In one embodiment, the inhibitors of the L-type $Ca^{2+}$ channel $\beta_3$ subunit are identified by the methods of the invention, as described above.

In a further embodiment of this aspect of the invention, the one or more L-type $Ca^{2+}$ channel $\beta_3$ subunit inhibitors is selected from the group consisting of antibodies selective for the L-type $Ca^{2+}$ channel $\beta_3$ subunit; antisense oligonucleotides directed against the L-type $Ca^{2+}$ channel $\beta_3$ subunit, and small interfering RNAs directed against the L-type $Ca^{2+}$ channel $\beta_3$ subunit.

Antibodies selective for the L-type $Ca^{2+}$ channel $\beta_3$ subunit can be polyclonal or monoclonal antibodies, and include chimeric, single chain and humanized antibodies, as well as Fab fragments, or the product of an Fab expression library. In a preferred embodiment, the antibodies are selective for an L-type $Ca^{2+}$ channel $\beta_3$ subunit as disclosed in SEQ ID NO:2, SEQ ID NO:4, and/or SEQ ID NO:6. An antibody is considered to selectively bind to the L-type $Ca^{2+}$ channel $\beta_3$ subunit, even if it also binds to other proteins that are not substantially homologous with the L-type $Ca^{2+}$ channel 3 subunit. Such antibodies can be made by standard methods in the art, such as described in Harlow and Lane, Antibodies; A Laboratory Manual, Cold Spring Harbor Laboratory, Cold Spring Harbor, N.Y., (1988). Full-length protein or antigenic peptide fragments of the L-type $Ca^{2+}$ channel $\beta_3$ subunit can be used as an immunogen to generate antibodies using standard techniques for polyclonal and monoclonal antibody preparation.

In one example, pre-immune serum is collected prior to the first immunization. A peptide portion of the amino acid sequence of an L-type $Ca^{2+}$ channel $\beta_3$ subunit, together with an appropriate adjuvant, is injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against L-type $Ca^{2+}$ channel $\beta_3$ subunit can then be purified directly by passing serum collected from the animal through a column to which non-antigen-related proteins prepared from the same expression system without L-type $Ca^{2+}$ channel $\beta_3$ subunit bound.

Monoclonal antibodies can be produced by obtaining spleen cells from the animal. (See Kohler and Milstein, Nature 256, 495-497 (1975)). In one example, monoclonal antibodies (mAb) of interest are prepared by immunizing inbred mice with a L-type $Ca^{2+}$ channel $\beta_3$ subunit, or portion thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations by the intravenous (IV) route. Lymphocytes from antibody positive mice are obtained by removing spleens from immunized mice by standard procedures known in the art. Hybridoma cells are produced by mixing the splenic lymphocytes with an appropriate fusion partner under conditions that allow formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

To generate such an antibody response, an L-type $Ca^{2+}$ channel $\beta_3$ subunit or antigenic portion thereof is typically formulated with a pharmaceutically acceptable carrier for parenteral administration. Such acceptable adjuvants include, but are not limited to, Freund's complete, Freund's incomplete, alum-precipitate, water in oil emulsion containing *Corynebacterium parvum* and tRNA. The formulation of such compositions, including the concentration of the polypeptide and the selection of the vehicle and other components, is within the skill of the art.

Antibodies can be fragmented using conventional techniques, and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments.

In another preferred embodiment, the L-type $Ca^{2+}$ channel $\beta_3$ subunit inhibitors for use with the methods of the present invention are oligomeric compounds, particularly antisense oligonucleotides. Such antisense oligonucleotides are used for inhibiting the expression and/or function of nucleic acid molecules encoding the L-type $Ca^{2+}$ channel 3 subunit, and thus ultimately inhibiting the amount of L-type $Ca^{2+}$ channel $\beta_3$ subunit produced. This is accomplished by providing antisense oligonucleotides that specifically hybridize with one or more nucleic acids encoding the L-type $Ca^{2+}$ channel $\beta_3$ subunit. Such nucleic acids encompass DNA encoding the L-type $Ca^{2+}$ channel $\beta_3$ subunit, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds that specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is inhibition of the expression of the L-type $Ca^{2+}$ channel $\beta_3$ subunit.

The target is a nucleic acid molecule encoding the L-type $Ca^{2+}$ channel $\beta_3$ subunit, such as those encoding the proteins of SEQ ID NOS: 2, 4, and/or 6. In a preferred embodiment, the antisense oligonucleotides target a nucleic acid selected from the group consisting of SEQ ID NOS: 1, 3, and 5, or portions thereof. In a most preferred embodiment, the antisense oligonucleotides target the human L-type $Ca^{2+}$ channel $\beta_3$ subunit gene [SEQ ID NO:5] (GenBank accession number L27584), or portions thereof.

Preferred intragenic sites in the target gene include sites comprising the translational initiation codon, the termination codon, the coding region, intron-exon junctions, and the untranslated regions (both 5' and 3').

As used herein, "hybridization" means hydrogen bonding, which may be Watson-Crick, Hoogsteen or reversed Hoogsteen hydrogen bonding, between complementary nucleoside or nucleotide bases. The oligonucleotide and the DNA or RNA are complementary to each other when a sufficient number of corresponding positions in each molecule are occupied by nucleotides which can hydrogen bond with each other. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

The antisense compounds in accordance with this invention preferably comprise from about 8 to about 50 nucleotides or nucleosides. Particularly preferred antisense compounds are antisense oligonucleotides, even more preferably those comprising from about 12 to about 30 nucleotides or nucleosides. Antisense compounds include ribozymes, external guide sequence (EGS) oligonucleotides (oligozymes), and other short catalytic RNAs or catalytic oligonucleotides which hybridize to the target nucleic acid and modulate its expression.

While antisense oligonucleotides are a preferred form of antisense compound, the present invention comprehends other oligomeric antisense compounds, including but not limited to oligonucleotide mimetics such as are described below. Specific examples of preferred antisense compounds useful in this invention include oligonucleotides containing modified backbones or non-natural internucleoside linkages. As defined in this specification, oligonucleotides having modified backbones, include, but are not limited to, phosphorothioates, chiral phosphorothioates, phosphorodithioates, phosphotriesters, aminoalkylphosphotriesters, methyl and other alkyl phosphonates, phosphinates, phosphoramidates, thionophosphoramidates, thionoalkylphosphonates, thionoalkylphosphotriesters, selenophosphates and boranophosphates. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

Other modified oligonucleotide backbones include short chain alkyl or cycloalkyl internucleoside linkages, mixed heteroatom and alkyl or cycloalkyl internucleoside linkages, or one or more short chain heteroatomic or heterocyclic internucleoside linkages. Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

One example of an oligonucleotide mimetic that can be used is referred to as a peptide nucleic acid (PNA). In PNA compounds, the sugar-backbone of an oligonucleotide is replaced with an amide containing backbone, in particular an aminoethylglycine backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., Science, 1991, 254, 1497-1500.

Oligonucleotides may also include base modifications or substitutions, including, but not limited to, 5-substituted pyrimidines, 6-azapyrimidines and N-2, N-6 and O-6 substituted purines. Representative United States patents that teach the preparation of such modified bases include, but are not limited to, U.S. Pat. Nos. 3,687,808; 4,845,205; 5,130,302; 5,134,066; 5,175,273; 5,367,066; 5,432,272; 5,457,187;

5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941.

Other modifications of oligonucleotides for use in the methods of the invention involve chemically linking to the oligonucleotide one or more moieties or conjugates that enhance the activity, cellular distribution or cellular uptake of the oligonucleotide, including but not limited to intercalators, reporter molecules, polyamines, polyamides, polyethylene glycols, polyethers, and groups that enhance the pharmacodynamic properties of oligomers, and groups that enhance the pharmacokinetic properties of oligomers. Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Where the oligonucleotides contain such modifications, it is not necessary for all positions in a given oligonucleotide to be uniformly modified, and in fact more than one of the aforementioned modifications may be incorporated in a single oligonucleotide or even at a single nucleoside or nucleotide within an oligonucleotide.

The antisense compounds used in accordance with this invention may be routinely produced by the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

In a further embodiment, the inhibitors of the L-type $Ca^{2+}$ channel $\beta_3$ protein are small interfering RNA ("siRNA") sequences directed against the L-type $Ca^{2+}$ channel $\beta_3$ nucleic acid. Double-stranded (dsRNA) directs the sequence-specific degradation of mRNA through a process known as RNA interference (RNAi). (US Application 20020086356.) It is preferred that 21-23 nucleotide dsRNA fragments derived from the L-type $Ca^{2+}$ channel $\beta_3$ are used to inhibit L-type $Ca^{2+}$ channel $\beta_3$ expression, although longer or shorter dsRNA sequences can be used. In a preferred embodiment, the dsRNA fragments are directed at a sequence selected from the group consisting of SEQ ID NO:1, SEQ ID NO:3, and SEQ ID NO:5, or fragments thereof. The molecules can be blunt ended or comprise overhanging ends (e.g., 5', 3') of from 1 to 6 nucleotides. Such siRNA sequences can be prepared using standard techniques, such as chemical synthesis or recombinant production.

Dosing for the therapeutic methods of the invention are dependent on severity and responsiveness of the disease state to be treated, with the course of treatment lasting from several days to several months, or until a cure is effected or a diminution of the disease state or symptoms thereof are achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual inhibitors, and can generally be estimated based on EC50 found to be effective in in vitro and in vivo animal models. In general, dosage is from 0.01 ug to 100 mg per kg of body weight, and may be given once or more daily, weekly, or otherwise. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the inhibitor is administered in maintenance doses, similar to those described above.

In another aspect, the present invention also includes pharmaceutical compositions comprising one or more inhibitor of the L-type $Ca^{2+}$ channel $\beta_3$ subunit and a pharmaceutically acceptable carrier. In a preferred embodiment, the one or more inhibitor of the L-type $Ca^{2+}$ channel $\beta_3$ subunit is selected from the group consisting of an antibody selective for the L-type $Ca^{2+}$ channel $\beta_3$ subunit; an antisense oligonucleotide directed against the L-type $Ca^{2+}$ channel $\beta_3$ subunit; and a small interfering RNA directed against the L-type $Ca^{2+}$ channel $\beta_3$ subunit, as discussed above. In other embodiments, the inhibitor is one identified according to the drug discovery methods of the invention.

The inhibitors may be subjected to conventional pharmaceutical operations such as sterilization and/or may contain conventional adjuvants, such as preservatives, stabilizers, wetting agents, emulsifiers, buffers etc. In another preferred embodiment, the inhibitors are identified by the methods of the invention.

For administration, the inhibitors are ordinarily combined with one or more adjuvants appropriate for the indicated route of administration. The inhibitors may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the inhibitors may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The inhibitors may be made up in a solid form (including granules, powders or suppositories) or in a liquid form (e.g., solutions, suspensions, or emulsions). Suitable solutions for use in accordance with the invention are sterile, dissolve sufficient amounts of the polypeptides, and are not harmful for the proposed application.

The present invention may be better understood in light of the following examples. The examples are intended to further illustrate certain preferred embodiments of the invention, and are not intended to limit the scope of the invention.

EXAMPLES

Example 1

Preparation of L-type $Ca^{2+}$ Channel $\beta_3$ Knockout Mice

Figure 1B:
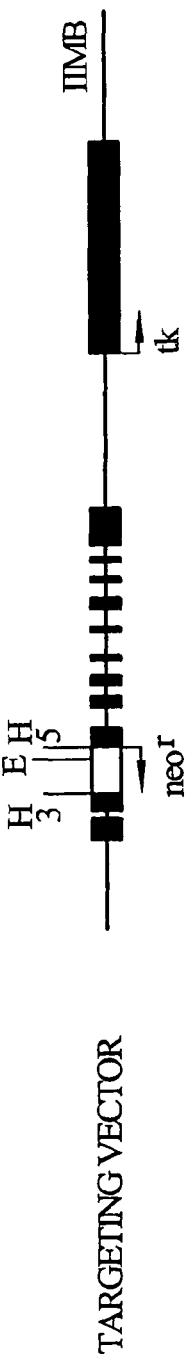
Figure 1C:
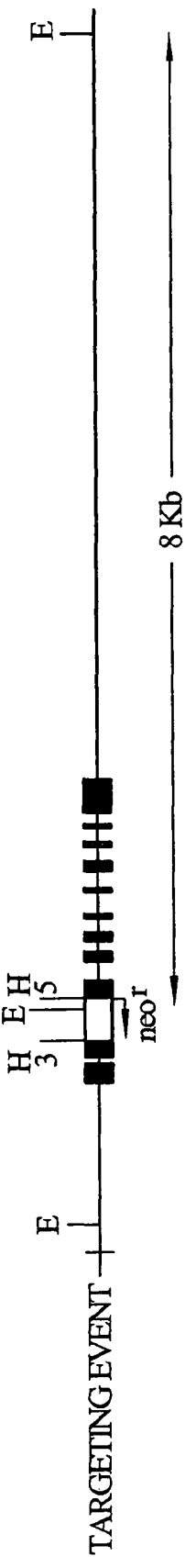

The $\beta_3$ gene (Murakami, M. et al. 1996 *Eur. J. Biochem.* 236:138-143 1996) was knocked-out ($\beta_3^{-/-}$) by replacing part of its exon 3 and the complete exon 4 with a neomycin-resistance gene (neo). Targeting vector IIMB was prepared, starting with the pMCl neoPolyA vector (Stratagene) by replacing a 1 kb HincII (H) fragment, containing part of exon 3, exon 4, and part of the following intron of the mouse 3 gene, with the neomycin resistance cassette (neo$^r$). (See FIG. 1.)

For generation of $\beta_3^{-/-}$ mice, linearized targeting constructs were electroporated into R1 embryonic stem (ES) cells (Nagy, A. et al. 1993, *Proc. Natl. Acad. Sci. USA* 90:8424-8428) and recombinant clones were selected with G418 and ganciclovir. Three out of 470 ES cell clones with predicted genomic structures for the targeting vector IIMB were identified and selected. Selected ES cell clones were microinjected into C57BL/6 blastocysts and transferred into the uteri of pseudopregnant recipient females. Two of three homologous recombinant clones were injected into C57BL/6 mouse blastocysts. Chimeric mice were mated with C57BL/6 females.

Offsprings were typed for the $\beta_3$ mutation by Southern blot analysis. Genomic DNA from ES cells or mouse tails were digested with EcoRI, separated on agarose gel and transferred to nylon membrane. Hybridizations were carried out with a $^{32}$P-labeled probe (~500 bp SmaI/ApaI fragment). After hybridization, the blots were washed and exposed to X-ray films. A polymerase chain reaction based assay was developed for rapid offspring-genotyping using the primer pair 5'-AGC ACA AAC CTG TGG CAT TTG-3' (covering nucleotides 167-187 of exons 2 and 3 of the murine $\beta_3$ gene) [SEQ ID NO:7] and 5'-TCG GTT GCC AAT GTC ACC CAG-3' (covering nucleotides 430-450 of exon 5 of the murine $\beta_3$ gene) [SEQ ID NO: 8] and mouse tail genomic DNA as template.

Wild-type and mutant alleles were indicated by the presence of a 12 kb and a 8 kb EcoRI fragment, respectively. The deletion of the $\beta_3$ gene was confirmed by Northern blot analysis and immunoblotting of brain extracts. Breeding of heterozygous mice generated $\beta_3^{-/-}$ mice at a rate as expected from the mendelian frequency (118+/+, 212+/−, 99−/−). Surviving homozygotes grew normally, lived longer than one year, were fertile and had no obvious symptoms.

Example 2

Glucose Tolerance of L-Type $Ca^{2+}$ Channel $\beta_3$ Knockout Mice

Intraperitoneal and oral glucose tolerance tests were carried out on the L-type $Ca^{2+}$ channel $\beta_3$ knockout mice. For the intraperitoneal glucose tolerance tests, 2 g D-glucose per kg bodyweight were injected intraperitoneally. For the oral glucose tolerance tests, mice were given 1.2 g glucose per kg bodyweight. In both glucose tolerance tests, blood samples were collected by tail bleeds.

Figure 2B:
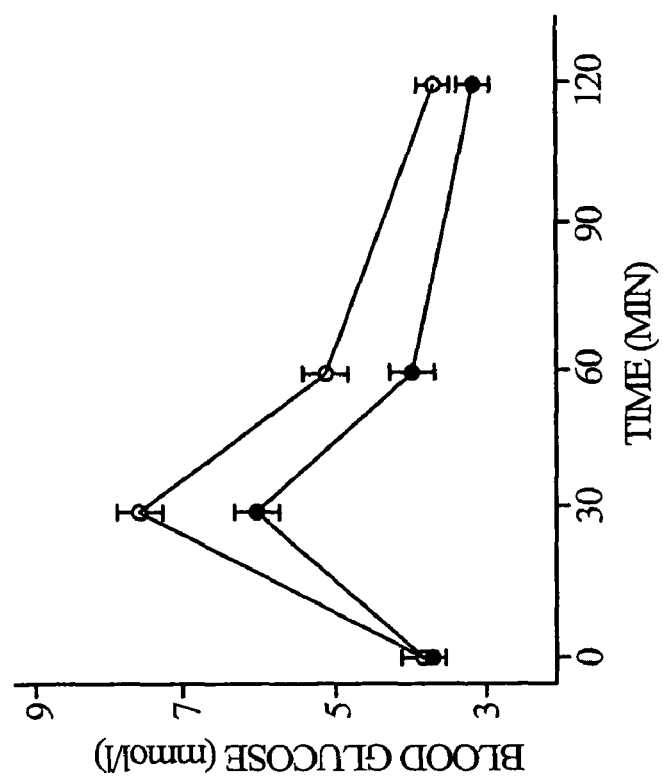
FIG. 2 depicts the results of the (A) intraperitoneal glucose tolerance test and (B) oral glucose tolerance test in wild type (○) and $\beta_3^{-/-}$ (●) mice.
Figure 2A:
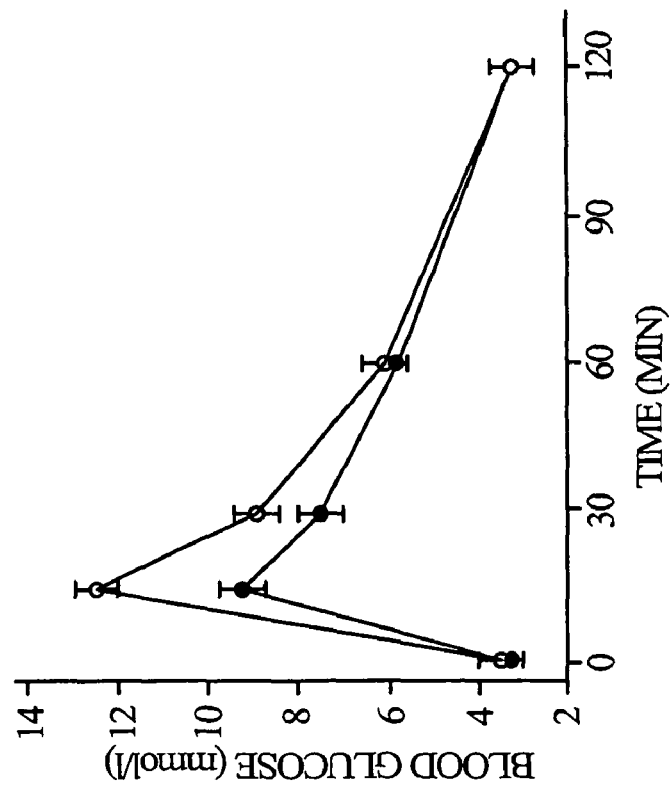

There was no significant difference in fasting blood glucose levels, however $\beta_3^{-/-}$ mice demonstrated a more efficient glucose homeostasis, exemplified by the more effective glucose removal from the blood, compared to wild type mice. (See FIG. 2).

Example 3

Insulin Release in Isolated $\beta_3$ Subunit Deficient Isolated Pancreatic Islets Islets of Langerhans were isolated by collagenase digestion and maintained overnight in RPMI 1640 culture medium (Flow Laboratories, UK). Single cells, obtained by shaking the islets in $Ca^{2+}$-free medium, were seeded into plastic dishes. For measurements of insulin release, islets were pre-incubated in Krebs-Ringer bicarbonate buffer (KRBB) for 30 min at 37° C. Groups of 3 islets were transferred to tubes containing 0.3 ml KRBB with test substances and incubated for another 30 min at 37° C. The incubation was terminated by cooling the samples on ice. Samples were stored at −20° C. until insulin was analyzed. There was no difference in insulin secretion at basal glucose concentration (3.3 mM glucose), whereas at stimulatory concentrations of the sugar (16.7 mM glucose) islets from $\beta_3^{-/-}$ mice showed significantly higher insulin release, approximately 200%, compared to islets from wild type mice.

To clarify whether the $\beta_3$ subunit directly affects the exocytotic machinery, insulin release from electropermeabilized islets at basal and elevated $Ca^{2+}$-concentrations was investigated. To measure insulin release from permeabilized islets, islets were washed in a cold permeabilization buffer. Islets were subsequently electropermeabilized in this buffer by 6 pulses of a 3 kV/cm electric field. Groups of 3 permeabilized islets were selected and transferred to tubes with 0.3 ml of a modified permeabilization buffer containing 2 mM MgATP, 2 mM creatine phosphate, 10 U/ml creatine phosphokinase and a free $Ca^{2+}$ concentration of either 30 nM or 10 μM. Islets were incubated for 20 min at 37° C. Insulin was measured by radioimmunoassay, using rat insulin as a standard (Novo Nordisk, Denmark). No difference in insulin secretion between islets from $\beta_3^{-/-}$ and wild type mice was observed under any of these conditions.

Pancreatic islets from wild type and $\beta_3^{-/-}$ mice were transfected with adenovirus vectors encoding either GFP without the $\beta_3$ subunit or $\beta_3$-CFP. Insulin secretion was measured in response to 16.7 mM glucose at 24 h after transduction. Transduction by the $\beta_3$-encoding adenoviral expression construct back to $\beta_3$ subunit deficient islets changed the pattern of glucose-induced insulin release to that observed in wild-type islets.

Hence, the more efficient glucose homeostasis observed in $\beta_3^{-/-}$ mice is explained by an increased insulin release. There was no difference in glucose metabolism between wild type islets and islets from $\beta_3^{-/-}$ mice, as indicated from measurements of NAD(P)H fluorescence.

Example 4

Patch-Clamp Measurements

Cell-attached single-channel recordings were made in β-cells from wild type and $\beta_3$ subunit knockout mice with pipettes containing (in mM): 110 $BaCl_2$, 10 TEA-Cl and 5

HEPES-Ba(OH)$_2$ (pH 7.4). Currents resulting from voltage pulses (from −70 to 0 mV, 200 ms, 0.5 Hz) were filtered at 1 kHz, digitized at 5 kHz and registered. Whole-cell Ca$^{2+}$ currents were recorded in β-cells from wild type and β$_3$ subunit knockout mice by using the perforated-patch variant of whole-cell patch-clamp recording technique. Electrodes were filled with: 76 mM Cs$_2$SO$_4$, 1 mM MgCl$_2$, 10 mM KCl, 10 mM NaCl, and 5 mM Hepes (pH 7.35), as well as amphotericin B (0.24 mg/ml). The cells were bathed in a solution containing: 138 mM choline chloride, 10 mM tetraethylammonium chloride, 10 mM CaCl$_2$, 5.6 mM KCl, 1.2 mM MgCl$_2$, 5 mM HEPES and 3 mM glucose (pH 7.4). Whole-cell currents induced by voltage pulses (from a holding potential of −70 mV to several clamping potentials from −60 to 50 mV in 10 mV increments, 100 ms, 0.5 Hz) were filtered at 1 kHz and recorded. All recordings were made with an Axopatch 200 amplifier (Axon Instruments, Foster City, Calif.) at room temperature (about 22° C.). Acquisition and analysis of data were done using the software program pCLAMP6 (Axon Instruments, Foster City, Calif.).

The whole-cell configuration of the patch-clamp technique was performed as follows: pipettes were pulled from borosilicate glass, coated with Sylgard near the tips and fire-polished. The pipettes (2-5 mΩ) were filled with a solution containing 150 mM N-methyl-D-glucamine, 125 mM HCl, 1.2 mM MgCl$_2$, 10 mM EGTA, 5 mM HEPES and 3 mM MgATP. pH was adjusted to 7.15 with KOH. Bath buffer contained (in mM) NaCl 138, KCl 5.6, MgCl$_2$ 1.2, CaCl$_2$ 10, HEPES 5 and pH 7.4. Islets or isolated cells were loaded with 2 µM fura 2/AM for 30 min in KRBB. For measurements of CCh (carbamylcholine) effects in Ca$^{2+}$-free medium, KRBB containing no Ca$^{2+}$ and 100 µM EGTA was used. After loading, a single islet or cells attached to a coverslip were transferred to an open perfusion chamber and maintained at 37° C. Measurements of 340/380 nm fluorescence ratio, reflecting [Ca$^{2+}$]$_i$, were done as described in the art (Zaitsev, S. V. et al. 1995, *Proc. Natl. Acad. Sci. USA* 92:9712-9716). Time constant of decay in [Ca$^{2+}$]$_i$ was calculated with a double exponential decay equation using quasi Newton algorithm (Statistica for Windows, v. 5.0, StatSoft, Inc., USA). For measurements of [Ca$^{2+}$]$_{ER}$, the low affinity Ca$^{2+}$-sensitive fluorescent dye X-Rhod-5N (Molecular Probes) was employed. The K$_D$ of the dye (350 µM) guaranteed that the recorded changes in fluorescence mainly reflected changes in [Ca$^{2+}$]$_{ER}$. Single #1-cells were incubated with 5 µM X-Rhod-5N/AM for 1 hour at 4° C. to ensure dye loading into intracellular compartments. After loading, the cells were washed in dye free buffer and further incubated for 2 hours at 37° C. to remove the dye from the cytosol. X-Rhod-5N was excited at 570 nm and signal was collected through a 600 nM long pass emission filter.

Exocytosis was monitored in single β-cells as changes in cell membrane capacitance, using the perforated-patch whole-cell configuration. Changes in cell capacitance were measured at a holding potential of −70 mV and detected using software written in Axobasic (Axon Instruments, Foster City, Calif., USA). During the experiments the cells, placed in an experimental chamber with a volume of 0.4 ml, were continuously superfused at a rate of 1.5 ml/min to maintain the temperature at 33° C. Experiments commenced when two successive depolarizations applied at 2 min interval elicited exocytotic responses of the same amplitude (∀10%) to ascertain that the observed changes were not simply attributed to spontaneous long-term changes of the secretory capacity. The pipette solution contained 76 mM Cs$_2$SO$_4$, 10 mM NaCl, 10 mM KCl, 1 mM MgCl$_2$ and 5 mM HEPES (pH 7.35 with CsOH). Electrical contact with the cell interior was established by adding 0.24 mg/ml amphotericin B to the pipette solution. Perforation required a few minutes and the voltage-clamp was considered satisfactory when the series conductance (G$_{series}$) was constant and >35-40 nS. The extracellular medium consisted of 118 mM NaCl, 20 mM tetraethylammonium-Cl (TEA-Cl), 5.6 mM KCl, 1.2 mM MgCl$_2$, 2.6 mM CaCl$_2$, 5 mM HEPES (pH 7.40 using NaOH) and 5 mM D-glucose. Parallel measurements of [Ca$^{2+}$]$_i$ were made using fura-2/AM and fluorescence imaging Ionoptix (Milton, Mass., USA). Calibration of the fluorescence ratios was performed by using the standard whole-cell configuration to infuse fura-2 with different mixtures of Ca$^{2+}$ and EGTA having a known [Ca$^{2+}$]$_i$.

Example 5

Molecular Mechanisms Underlying Increased Insulin Release in Response to Glucose in L-Type Ca$^{2+}$ Channel β$_3$ Knockouts The possible molecular mechanisms underlying the more pronounced insulin release in response to glucose in β$_3$$^{-/-}$ mice were investigated. Cell-attached single-channel recordings were made to compare biophysical properties of the β-cell voltage-gated L-type Ca$^{2+}$ channel in β$_3$$^{-/-}$ mice with those in wild type mice. Ba$^{2+}$ currents flowing through single Ca$^{2+}$ channels recorded from a patch attached to a β-cell lacking the β$_3$ subunit did not differ markedly from those obtained in a wild type β-cell. Single channel parameter analysis shows no striking difference in mean open time, open probability and availability between wild type and β$_3$$^{-/-}$ mice. The data on single channel recordings indicate that removal of the β$_3$ subunit does not influence biophysical properties of the voltage-gated L-type Ca$^{2+}$ channel in the β-cell.

The above results do not exclude the possibility that removal of the β$_3$ subunit alters the number of L-type Ca$^{2+}$ channels in the plasma membrane. Therefore, perforated whole-cell recordings of the activity of voltage-gated L-type Ca$^{2+}$ channels were performed (Hamill, O. P. et al. 1981, *Pflügers Arch*. 391:85-100). There was no significant difference in Ca$^{2+}$ current density between β$_3$$^{-/-}$ and wild type β-cells. These results show that the β-cell lacking the β$_3$ subunit expresses a similar number of L-type Ca$^{2+}$ channels in the plasma membrane as the wild type β-cell. Thus other β subunits can substitute for the β$_3$ subunit in maintaining number and function of L-type Ca$^{2+}$ channels in the β-cell plasma membrane. Moreover, the more pronounced insulin release in response to glucose in β$_3$$^{-/-}$ mice cannot be explained by an increased L-type Ca$^{2+}$ channel activity.

Changes in [Ca$^{2+}$]$_i$ were next evaluated. Subsequent to stimulation with high glucose, there was no difference in either amplitude or time course of the initial increase in [Ca$^{2+}$]$_i$ between β-cells from β$_3$$^{-/-}$ and wild type mice. The changes in [Ca$^{2+}$]$_i$ subsequent to the initial increase were categorized into three groups: slow oscillations (period of approximately 160 seconds), fast oscillations (period of approximately 10 seconds) and no oscillations. In wild type mice, 43 recordings (43 islets) were made. Fast oscillations were observed in 19% and slow oscillations were observed in 35% of these islets. The remaining 46% of the islets showed no oscillations. In β$_3$$^{-/-}$ mice, 71% of 42 recordings showed fast oscillations, 14% showed slow oscillations and the remaining 15% exhibited no oscillatory pattern. The total increase in [Ca$^{2+}$]$_i$, measured as area under the curve, was not different in islets from β$_3$$^{-/-}$ and wild type mice. Thus, with regard to glucose-induced changes in [Ca$^{2+}$]$_i$, the only parameter differing between islets obtained from $\beta_3^{-/-}$ and control mice was the number of islets exhibiting high-frequency $[Ca^{2+}]_i$ oscillations.

In the pancreatic β-cell, $[Ca^{2+}]_i$ oscillations are dependent upon a complex interplay between $Ca^{2+}$- and $K^+$-conductances of plasma membrane and ER channels (Berggren & Larsson 1994, Biochem. Soc. Transact. 22:12-18; Roe et al. 1993, J. Biol. Chem. 268:9953-9956). The levels of inositol 1,4,5-trisphosphate ($InsP_3$) increase subsequent to stimulation of the phospholipase C (PLC) system, resulting in mobilization of $Ca^{2+}$ from the ER. Treatment of β-cells with thapsigargin, an inhibitor of the endoplasmic reticulum (ER) $Ca^{2+}$-ATPase, is known to transform $[Ca^{2+}]_i$ oscillations into a monophasic elevation in $[Ca^{2+}]_i$ (Roe et al. 1998, J. Biol. Chem. 273:10402-10410). Accordingly, 30 min preincubation of islets from both wild type and $\beta_3^{-/-}$ mice with 1 μM thapsigargin prevented glucose-induced oscillations in $[Ca^{2+}]_i$. Blocking the $InsP_3$-receptor with 2-aminoethoxy-diphenyl borane (2-APB) transformed $[Ca^{2+}]_i$ oscillations from fast into slow in β-cells from $\beta_3^{-/-}$ mice. Hence, oscillations in $[Ca^{2+}]_i$ in the $\beta_3^{-/-}$ β-cell are also dependent on $Ca^{2+}$ flux through the $InsP_3$-sensitive ER $Ca^{2+}$ store.

That insulin release in response to glucose in islets treated with thapsigargin was no different in control and $\beta_3^{-/-}$ mice suggests a direct link between increased glucose-induced insulin secretion and the higher frequency in $[Ca^{2+}]_i$ oscillatory pattern seen in islets from $\beta_3^{-/-}$ mice. To further verify this notion, changes in $[Ca^{2+}]_i$ and insulin exocytosis were measured simultaneously, applying a depolarizing pulse protocol mimicking an oscillatory versus a monophasic increase in $[Ca^{2+}]_i$.

Simultaneous measurements of $[Ca^{2+}]_i$ and changes in cell capacitance ($C_m$), the latter as a measure of insulin exocytosis, were made in a single voltage-clamped β-cell before, during and after a 1 min membrane depolarisation from −70 mV to −40 mV. In a series of five experiments, the membrane depolarization to −40 mV increased $[Ca^{2+}]_i$ from a basal of 116∇21 nM to 575∇43 nM (P<0.01), which decayed to 133∇37 nM (P<0.01) upon returning to the holding potential of −70 mV. This elevation in $[Ca^{2+}]_i$, while not being sufficient to evoke secretion by itself, transiently increased the exocytotic capacity of the β-cells and the amplitude of the capacitance increases elicited by voltage-clamp depolarizations to 0 mV rose by 71∇12% (P<0.05; n=5) over that seen prior to the 1 min depolarization to −40 mV. These increases in cell capacitance were relatively small compared to those observed after a series of voltage-clamp depolarizations, over a period of 1 min, to 0 mV (100 ms duration; 10 Hz). Under these conditions, $[Ca^{2+}]_i$ increased from 138∇27 nM to 438∇47 nM (P<0.01), which decayed to 156∇39 nM (P<0.01) upon returning to the holding potential of −70 mV. Again, this elevation in $[Ca^{2+}]_i$ was not associated with a change in cell capacitance, but increased the exocytotic capacity of the β-cells by 309∇27% (P<0.005; n=5) over that seen prior to the train of depolarizations. The changes in exocytotic capacity were not associated with a change in the integrated $Ca^{2+}$ current in response to the 500 ms depolarizations to 0 mV.

The role of the $InsP_3$-releasable intracellular $Ca^{2+}$-pool was investigated in order to elucidate the molecular mechanisms underlying the enhanced $[Ca^{2+}]_i$ oscillation frequency in $\beta_3^{-/-}$ β-cells. The $Ca^{2+}$-pool was depleted either by omission of $Ca^{2+}$ from outside of the cell or treatment of the cell with thapsigargin in the absence of extracellular $Ca^{2+}$, and the increase in $[Ca^{2+}]_i$ subsequent to the addition of 2.5 mM extracellular $Ca^{2+}$ was investigated.

Under these experimental conditions, the increase in $[Ca^{2+}]_i$ is in part reflecting ER $Ca^{2+}$ release due to a cooperative activation of $InsP_3$ receptors by sequential binding of $InsP_3$ and $Ca^{2+}$. The more pronounced $[Ca^{2+}]_i$ increase observed in islets from $\beta_3^{-/-}$ mice compared to wild type mice, irrespective of depletion protocol, reflect the existence of more releasable $Ca^{2+}$ in the $InsP_3$ sensitive pool in β-cells lacking the $\beta_3$ subunit. Application of 2 μM gadolinium did not affect this increase in $[Ca^{2+}]_i$ suggesting that it is not accounted for by traditional capacitative $Ca^{2+}$ entry (Hoth, M. et al. 1993, J. Physiol. 465:359-86).

Carbamylcholine (CCh)-induced activation of PLC produced a transient increase in $[Ca^{2+}]_i$ in islets from both $\beta_3^{-/-}$ and wild type mice. The peak in $[Ca^{2+}]_i$ increase was higher and the decline in $[Ca^{2+}]_i$ following the initial peak was faster in islets from $\beta_3^{-/-}$ compared to wild type mice. To clarify the dependency of this $[Ca^{2+}]_i$ peak on extracellular $Ca^{2+}$, the effect of CCh was studied in islets incubated in $Ca^{2+}$-free medium. Under these conditions there was no significant difference in CCh-induced elevations in $[Ca^{2+}]_i$.

To evaluate a possible difference between fl-cells obtained from wild type and $\beta_3^{-/-}$ mice in handling of ER $Ca^{2+}$ ($[Ca^{2+}]_{ER}$), X-Rhod-5N, a low-affinity fluorescent $Ca^{2+}$ dye, was used for measurements of $[Ca^{2+}]_{ER}$. Following stimulation with CCh there was a slower depletion of $[Ca^{2+}]_{ER}$ in β-cells obtained from $\beta_3^{-/-}$—compared to wild type mice. Hence, there is ample experimental support for the notion that the $InsP_3$-releasable intracellular $Ca^{2+}$-pool is larger in $\beta_3^{-/-}$ compared to wild type β-cells.

It is known in the art that the β-cell exhibits $InsP_3$-mediated periodic increases in $[Ca^{2+}]_i$ (Ämmälä, C. et al 1991, Nature 353:849-852) and this mechanism is likely to be involved in the regulation of the glucose-induced oscillatory $[Ca^{2+}]_i$ responses. The $\beta_3$ subunit is now demonstrated to be associated with the $InsP_3$ receptor, negatively modulating $InsP_3$-induced $Ca^{2+}$ release. Removal of the $\beta_3$ subunit is compatible with the observed larger $InsP_3$-releasable $Ca^{2+}$-pool and enhanced $[Ca^{2+}]_i$ oscillation frequency. This may then constitute the molecular explanation to the increased glucose-induced insulin release in the $\beta_3^{-/-}$ mice.

We claim:

1. A method for identifying inhibitors of the L-type $Ca^{2+}$ channel $\beta_3$ protein, comprising:
   a) contacting recombinant host cells with a calcium indicator that emits detectable signals in the presence of calcium, wherein the recombinant host cells have been transfected with a recombinant expression vector comprising nucleic acid control sequences operatively linked to an L-type $Ca^{2+}$ channel $\beta_3$ protein-encoding nucleic acid sequence, wherein the contacting occurs under conditions to promote expression of the L-type $Ca^{2+}$ channel $\beta_3$ protein and wherein the host cell does not possess functional $\beta_3$ protein-containing L-type $Ca^{2+}$ channels after expression of the L-type $Ca^{2+}$ channel $\beta_3$ protein;
   b) treating the host cells with one or more test compounds, wherein the treating occurs before, simultaneous with, or after the contacting of the host cells with the calcium indicator;
   c) stimulating the recombinant host cells with an amount of ATP that is effective to increase intracellular calcium concentration release from cellular stores; and
   d) detecting signals from the calcium indicator in the recombinant host cells, wherein a test compound-induced increase in the signals from the calcium indicator in the recombinant host cells as compared to a control indicates that the test compound promotes release of calcium from intracellular stores, and wherein the test compound is an inhibitor of the L-type $Ca^{2+}$ channel $\beta_3$ protein.

2. The method of claim 1, wherein the method is used to identify compounds for use in treating one or more disorders selected from the group consisting of diabetes, insulin resistance, impaired insulin secretion, and impaired glucose homeostasis.

3. The method of claim 1 wherein the recombinant host cells are mammalian cells.

4. The method of claim 3 wherein the recombinant host cells are human cells.

5. The method of claim 1 wherein the L-type $Ca^{2+}$ channel $\beta_3$ protein-encoding nucleic acid sequence encodes the protein of SEQ ID NO:6.

6. The method of claim 5, wherein the recombinant host cells are human cells.

7. The method of claim 6, wherein the method is used to identify compounds for use in treating one or more disorders selected from the group consisting of diabetes, insulin resistance, impaired insulin secretion, and impaired glucose homeostasis.

8. The method of claim 6, wherein step (c) comprises stimulating the recombinant host cells with between 1 μM and 100 μM ATP.

\* \* \* \* \*